US011118220B2

(12) United States Patent
Daugharthy et al.

(10) Patent No.: US 11,118,220 B2
(45) Date of Patent: *Sep. 14, 2021

(54) METHOD AND APPARATUS FOR VOLUMETRIC IMAGING OF A THREE-DIMENSIONAL NUCLEIC ACID CONTAINING MATRIX

(71) Applicant: President and Fellows of Harvard College, Cambridge, MA (US)

(72) Inventors: Evan R. Daugharthy, Cambridge, MA (US); Richard C. Terry, Carlisle, MA (US); Je-hyuk Lee, Allston, MA (US); George M. Church, Brookline, MA (US); Benjamin W. Pruitt, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/386,337

(22) Filed: Apr. 17, 2019

(65) Prior Publication Data
US 2019/0241950 A1 Aug. 8, 2019

Related U.S. Application Data

(63) Continuation of application No. 15/969,118, filed on May 2, 2018, now Pat. No. 10,266,888, which is a continuation of application No. PCT/US2016/060279, filed on Nov. 3, 2016.

(60) Provisional application No. 62/250,182, filed on Nov. 3, 2015.

(51) Int. Cl.
*C12Q 1/68* (2018.01)
*C12Q 1/6869* (2018.01)
*C12Q 1/6841* (2018.01)

(52) U.S. Cl.
CPC ............ *C12Q 1/6869* (2013.01); *C12Q 1/68* (2013.01); *C12Q 1/6841* (2013.01)

(58) Field of Classification Search
CPC ...... C12Q 1/68; C12Q 1/6841; C12Q 1/6869; C12Q 2543/101; C12Q 2565/518; C12Q 2565/601
See application file for complete search history.

(56) References Cited

U.S. PATENT DOCUMENTS

| 4,123,610 | A | 10/1978 | Summerton et al. |
|---|---|---|---|
| 4,844,617 | A | 7/1989 | Kelderman et al. |
| 4,886,741 | A | 12/1989 | Schwartz |
| 4,981,985 | A | 1/1991 | Kaplan et al. |
| 5,151,189 | A | 9/1992 | Hu et al. |
| 5,563,056 | A | 10/1996 | Swan et al. |
| 5,594,235 | A | 1/1997 | Lee |
| 5,695,940 | A | 12/1997 | Drmanac et al. |
| 5,830,708 | A | 11/1998 | Naughton |
| 5,834,758 | A | 11/1998 | Trulson et al. |
| 5,871,921 | A | 2/1999 | Landegren et al. |
| 6,083,726 | A | 7/2000 | Mills, Jr. et al. |
| 6,306,597 | B1 | 10/2001 | Macevicz |
| 6,534,266 | B1 | 3/2003 | Singer |
| 6,586,176 | B1 | 7/2003 | Trnovsky et al. |
| 6,632,655 | B1 | 10/2003 | Mehta et al. |
| 7,255,994 | B2 | 8/2007 | Lao |
| 7,323,305 | B2 | 1/2008 | Leamon et al. |
| 7,427,479 | B2 | 9/2008 | Karger et al. |
| 7,473,767 | B2 | 1/2009 | Dimitrov |
| 7,745,129 | B1 | 6/2010 | Schatz |
| 7,906,285 | B2 | 3/2011 | Drmanac |
| 8,124,751 | B2 | 2/2012 | Pierce et al. |
| 8,268,554 | B2 | 9/2012 | Schallmeiner |
| 8,329,404 | B2 | 12/2012 | McKernan et al. |
| 8,460,865 | B2 | 6/2013 | Chee et al. |
| 8,501,459 | B2 | 8/2013 | Chen et al. |
| 8,551,710 | B2 | 10/2013 | Bernitz et al. |
| 9,201,063 | B2 | 12/2015 | Sood et al. |
| 9,217,151 | B2 | 12/2015 | Yin et al. |
| 10,138,509 | B2 | 11/2018 | Church et al. |
| 10,227,639 | B2 | 3/2019 | Levner et al. |
| 10,266,888 | B2 * | 4/2019 | Daugharthy ......... C12Q 1/6841 |
| 10,267,808 | B2 | 4/2019 | Cai |
| 10,494,662 | B2 | 12/2019 | Church et al. |
| 10,494,667 | B2 | 12/2019 | Chee |
| 10,545,075 | B2 | 1/2020 | Deisseroth et al. |
| 2002/0015952 | A1 | 2/2002 | Anderson et al. |
| 2002/0155989 | A1 | 10/2002 | Efimov et al. |
| 2002/0172950 | A1 | 11/2002 | Kenny et al. |
| 2003/0148335 | A1 | 8/2003 | Shen et al. |
| 2004/0077014 | A1 | 4/2004 | Becker |

(Continued)

FOREIGN PATENT DOCUMENTS

| EP | 2878671 A1 | 6/2015 |
|---|---|---|
| JP | 2012-170337 A | 9/2012 |

(Continued)

OTHER PUBLICATIONS

Chen et al., "Expansion microscopy," Science, vol. 347, No. 6221, pp. 543-548 (Jan. 30, 2015).
Chozinski et al., "Expansion microscopy with conventional antibodies and fluorescent proteins," Nature Methods, vol. 13, No. 6, pp. 485-488 (Jun. 1, 2016).
Chen et al., "Nanoscale imaging of RNA with expansion microscopy," Nature Methods, vol. 133, No. 8, pp. 679-684 (Aug. 1, 2016).
Supplemental Material for Schweitzer et al. (PNAS 2000; 97(18):10113-10119) (Year: 2000).
Dec. 18, 2014 (PCT) International Preliminary Report—App PCT/US2013/044241.
Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.

(Continued)

*Primary Examiner* — David C Thomas
(74) *Attorney, Agent, or Firm* — Banner & Witcoff, Ltd.

(57) ABSTRACT

Methods of volumetric imaging of a three-dimensional matrix of nucleic acids within a cell is provided. An automated apparatus for sequencing and volumetric imaging of a three-dimensional matrix of nucleic acids is provided.

37 Claims, 13 Drawing Sheets

(56) References Cited

U.S. PATENT DOCUMENTS

| | | |
|---|---|---|
| 2004/0248144 A1 | 12/2004 | Mir |
| 2004/0259190 A1 | 12/2004 | Naughton |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0233318 A1 | 10/2005 | Chee et al. |
| 2006/0024711 A1 | 2/2006 | Lapidus et al. |
| 2006/0077536 A1 | 4/2006 | Bromage et al. |
| 2006/0177833 A1 | 8/2006 | Brenner |
| 2006/0183107 A1 | 8/2006 | Melkonyan et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0206275 A1 | 9/2007 | Hemmer et al. |
| 2007/0231823 A1 | 10/2007 | McKernan et al. |
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0269068 A1 | 10/2008 | Church et al. |
| 2009/0005259 A1 | 1/2009 | Drmanac |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2010/0009868 A1 | 1/2010 | Yan et al. |
| 2010/0047924 A1 | 2/2010 | Webster et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0223585 A1 | 9/2011 | Gullberg et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0252686 A1 | 10/2012 | Umbarger et al. |
| 2012/0330636 A1 | 12/2012 | Albou |
| 2013/0017229 A1 | 1/2013 | Mooney et al. |
| 2013/0245096 A1 | 9/2013 | Abitbol |
| 2014/0049632 A1 | 2/2014 | Hemmer |
| 2014/0087378 A1 | 3/2014 | Chatre et al. |
| 2014/0087427 A1 | 3/2014 | Bujnicki et al. |
| 2014/0200146 A1 | 7/2014 | Xie et al. |
| 2014/0220587 A1 | 8/2014 | Green, Jr. et al. |
| 2014/0270435 A1 | 9/2014 | Dunn |
| 2015/0133319 A1 | 5/2015 | Fu et al. |
| 2016/0024555 A1 | 1/2016 | Church et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2017/0176338 A1 | 6/2017 | Wu et al. |
| 2017/0212983 A1 | 7/2017 | Cai et al. |
| 2018/0010166 A1 | 1/2018 | Pierce et al. |
| 2018/0051322 A1 | 2/2018 | Church et al. |
| 2018/0282787 A1 | 10/2018 | Walter et al. |

FOREIGN PATENT DOCUMENTS

| | | |
|---|---|---|
| KR | 20080003402 A | 1/2008 |
| WO | 9746704 A1 | 12/1997 |
| WO | 98/56955 A1 | 12/1998 |
| WO | 01/26708 A1 | 4/2001 |
| WO | 01/37266 A1 | 5/2001 |
| WO | 2003044229 A1 | 5/2003 |
| WO | 2004/104645 A2 | 12/2004 |
| WO | 2006/138257 A2 | 12/2006 |
| WO | 2007/001986 A2 | 1/2007 |
| WO | 2007076128 A2 | 7/2007 |
| WO | 2007086900 A2 | 8/2007 |
| WO | 2007/121489 A2 | 10/2007 |
| WO | 2007/123744 A2 | 11/2007 |
| WO | 2007/149696 A1 | 12/2007 |
| WO | 2008069973 A2 | 6/2008 |
| WO | 2008157696 A2 | 12/2008 |
| WO | 2009/046348 A1 | 4/2009 |
| WO | 2009046149 A1 | 4/2009 |
| WO | 2010080134 A1 | 7/2010 |
| WO | 2010/087325 A1 | 8/2010 |
| WO | 2011/143583 A1 | 11/2011 |
| WO | 2012005595 A2 | 1/2012 |
| WO | 2012/058638 A2 | 5/2012 |
| WO | 2012/110899 A2 | 8/2012 |
| WO | 2012150035 A1 | 11/2012 |
| WO | 2013/055995 A2 | 4/2013 |
| WO | 2014/048083 A1 | 4/2014 |
| WO | 2014/0163886 A1 | 10/2014 |
| WO | 2014/182528 A2 | 11/2014 |
| WO | 2015/118029 A1 | 8/2015 |
| WO | 2015/127183 A2 | 8/2015 |
| WO | 2016081740 A1 | 5/2016 |
| WO | 2017/161251 A1 | 9/2017 |

OTHER PUBLICATIONS

Benner et al. "Gene Expression analysis by massively parallel signature sequencing (MPSS) on microbead arrays". Nature Biotechnology, vol. 18, pp. 630-634 (Jun. 31, 2000).

Brenner, et al. "Gene expression analysis by massively parallel signature sequencing (MPSS) on microbead arrays". Nature Biotechnology vol. 18, pp. 630-634 (2000) doi:10.1038/76469.

Eliscovich et al. mRNA on the move: The road to its biological destiny. Journal of Biological Chemistry, vol. 288, No. 28, pp. 20361-20368, Jul. 2013, in press May 2013 (Year: 2013).

Extended European Seach Report issued in corresponding European Application No. 12860433.7, dated Aug. 13, 2015.

Ginart, P et al. RNA Sequencing In Situ. Nat Biotechnol. Jun. 2014, vol. 32, No. 6; pp. 543-544; DOI: 10.1038/nbt.2921.

Grompe (1993) Nature Genetics DOI: 10.1038/ng1093-111.

Han et al. "Quantum-dot-tagged microbeads for multiplexed optical coding of biomolecules". Nature Biotechnology, vol. 19, 99. 631-635 (Jul. 31, 2001).

International Search Report and Written Opinion issued in corresponding International Application No. PCT/US2012/071398, dated Apr. 8, 2013.

Jambhekar et al. Cis-acting determinants of asymmetric, cytoplasmic RNA transport. RNA, vol. 13, pp. 625-642, 2007 (Year: 2007).

Kalivas et al. famRCA-Race: A rolling circle amplification RACE for isolating a family of homologous cDNAs in one reaction . . . Preparative Biochemistry and Biotechnology, vol. 40, No. 3, pp. 177-187, Jul. 2010. (Year: 2010).

Lee, JH et al. Highly Multiplexed Subcellular RNA Sequencing In Situ. Science. Mar. 21, 2014, vol. 343, No. 6177; pp. 1360-1363; abstract; p. 1360, second column, second paragraph to third column, first paragraph; p. 1361, first column, first paragraph; p. 1363, first column, second paragraph to second column, first paragraph; DOI: 10.1126/science.1250212.

Matlin et al. Spatial expression of the genome: the signal hypothesis at forty. Nature Reviews. Molecular Cell Biology, vol. 12, No. 5, pp. 333-340, May 2011, Epub Apr. 2011. (Year 2011).

Meeks et al. Characterization of genes encoding poly(A) polymerases in plants: Evidence for duplication and functional specialization. PLoS One, vol. 4, No. 11, e8082, Nov. 2009, printed as pp. 1/10-10/10. (Year 2009).

Office Action issued for corresponding European Patent Application No. 12780609.9, dated Sep. 23, 2015.

Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year 2006).

(56) References Cited

OTHER PUBLICATIONS

Saliba, AE et al. Single-Cell RNA-Seq: Advances and Future Challenges. Nucleic Acids Res. Jul. 22, 2014, vol. 42, No. 14; pp. 8845-8860; DOI: 10.1093/nar/gku555.
Seo, et al. Four-color DNA sequencing by synthesis on a chip using photocleavable fluorescent nucleotides. Proceeding of the National Academy of Sciences, Apr. 2005, 102 (17) 5926-5931.
Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.
Singer-Kruger et al. Here, there, everywhere. RNA Biology, vol. 11, No. 8, pp. 1031-1039, Aug. 2014. (Year: 2014).
Thisse et al. "High-Resolution in situ hybridization to whole-mount zebrafish embryos" 2008. Nature Protocols. vol. 3 No. 1 pp. 59-69. DOI:10.1038/nprot.2007.514.
Thisse et al. 2008 Nature protocols vol. 3 No. 1 pp. 59-69. Doi:10.1038/nprot.2007.514.
Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year 2004).
Weis et al. Protein targeting to subcellular organelles via mRNA localization. Biochimica et Biophysica Acta, vol. 1833, pp. 260-273, 2013, available online Apr. 2012 (Year 2012).
Brown et al., Review Article : In situ Hybridization with Riboprobes : An Overview for Veterinary Pathologists. Veterinary Pathology 35 : 159-167 (Year: 1998).
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Choi et al.,Programmable in situ amplification for multiplexed imaging of mRNA expression. Nature Biotechnology 28 (11): 1208 (Year: 2010).
Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.
Hansen et al., Sensitive ligand-based protein quantification using immuno-PCR: A critical review of single-probe and proximity ligation assays. Biotechniques 56:217-228 (Year: 2014).
Ke et al: 11 In situ sequencing for RNA analysis in preserved tissue and cells 11 Nature Methods, vol. 10, No. 9, Jul. 14, 2013 (Jul. 14, 2013), pp. 857-860, XP055163946, ISSN: 1548-7091, DOI: 10.1038/nmeth.2563 * the whole document *.
Kuimelis et al., Cleavage properties of an oligonucleotide containing a bridged internucleotide 5-phosphorothioate RNA linkage. Nucleic Acids Research 23 (23) : 4753-4760 (Year: 1999).
Larsson, Chatarina; Grundberg, Ida; Sbderberg, Ola; Nilsson, Mats: 11 In situ detection and genotyping of individual mRNA molecules, Nature Methods, vol . 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012] * the whole document *.
Lee et al: "Highly Multiplexed Subcellular RNA Sequencing in Situ", Science, vol. 343, No. 6177, Feb. 27, 2014 (Feb. 27, 2014), pp. 1360-1363, XP055305772, us ISSN: 0036-8075, DOI: 10.1126/science.1250212.
Mag et al., Synthesis and selective cleavage of an oligodeoxynucleotide containing a bridged internucleotide 5'-phosphorothioate linkage. Nucleic Acids Research 19(7): 1437 (Year: 1991).
Mitra R. D. et al: 11 In situ localized amplification and contact replication of many individual DNA molecules 11 Nucleic Acids Research, Information Retrieval Ltd, GB, vol. 27, No. 24, Dec. 15, 1999 (Dec. 15, 1999), p. e34, XP002292358, ISSN: 0305-1048, DOI: 10.1093/NAR/27.24.E34 * abstract *.

Nadji et al.,"Photochemically and Photoenzymatically Cleavable DNA," J. Am. Chem. Soc. 1992, 114, 9266-9269.
Nuovo: "Co-labeling Using In Situ PCR: A Review "Journal of Histochemistry & Cytochemistry, vol. 49, No. 11, Nov. 1, 2001 (Nov. 1, 2001), pp. 1329-1339, XP055164942, ISSN: 0022-1554, DOI: 10.1177/002215540104901101 * the whole document *.
Richardson et al., Experimental and Theoretical Studies of Light-to-Heat Conversion and Collective Heating Effects in Metal Nanoparticle Solutions. Nano Letters 9(3) : 1139-1146 (Year: 2009).
Song et al., Hybridization chain reaction-based aptameric system for the highly selective and sensitive detection of protein. Analyst 137: 1396 (Year 2012).
Srinivas et al., On the biophysics and kinetics of toehold-mediated DNA strand displacement. Nucleic Acids Research 41 (22) : 10641-10658 (Year: 2013).
Weibrecht, Irene et al., "Simultaneous Visualization of Both Signaling Cascade Activity and End-Point Gene Expression in Single Cells", PLOS One, vol. 6, No. 5, May 25, 2011 (May 25, 2011).
Xiao et al., Single-step electronic detection of femtomolar DNA by target-induced strand displacement in an electrode-bound duplex. PNAS 103(45): 16677-16680 (Year: 2006).
Zhang et al., Dynamic DNA nanotechnology using strand-displacement reactions. Nature Chemistry 3 : 103-113 (Year: 2011).
Zhao et al., An electrochemical aptasensor based on hybridization chain reaction with enzyme-signal amplification for interferon-gamma detection. Biosensors and Bioelectronics 36: 129-134 (Year: 2012).
Cao, Yi et al.,"In-situ immuno-PCR to detect antigens," The Lancet, Sep. 16, 2000, pp. 1002-1003, vol. 356.
Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retrieved from the Internet: URL:http://dspace.mit.edu/bitstream/handle/1721.1/107103/971494098-MIT.pdf?sequence=1 [retreived on Feb. 20, 2019].
Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.
Extended European Search Report dated May 13, 2019 for EP Application No. 16862929.3.
Extended European Search Report dated May 21, 2019 for European Application No. 16862945.9.
International Search Report and Written Opinion based on PCT/US2018/027583 dated Jun. 29, 2018.
Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.
Sano, Takeshi et al. "Immuno-PCR: Very Sensitive Antigen Detection by Means of Specific Antibody-DNA conjugates," Science, Oct. 2, 1992, pp. 120-122, vol. 258.
Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.
Soderberg, Ola et al.,"Direct observation of individual endogenous protein complexes in situ by proximity ligation," Nature Methods, Dec. 2006, pp. 995-1000, vol. 3, No. 12, Nature Publishing Group.
Zhou et al. "In Situ Detection of Messenger RNA Using Digoxigenin-Labeled Oligonucleotides and Rolling Circle Amplification" Experimental and Molecular Pathology 70, 281-288 (2001).
Choi, Harry M.T. et al., "Next-Generation in Situ Hybridization Chain Reaction: Higher Gain, Lower Cost, Greater Durability" ACS Nano, vol. 8, No. 5, May 27, 2014 (May 27, 2014), pp. 4284-4294, XP055409053, US.
Extended European Search Report issued for EP Application No. 17790240.0 dated Sep. 4, 2019.
Ravan, Hadi, et al. "Isothermal RNA detection through the formation of DNA concatemers contiaining HRP-mimicking DNAzyimes on the surface of gold nanoparticles", Biosensors and Bioelectronics, Elsevier Science Ltd. UK, Amsterdam, NL, vol. 80, Jan. 18, 2016 (Jan. 18, 2016), pp. 67-73, XP029441324.

(56) References Cited

OTHER PUBLICATIONS

Amasino, "Acceleration of nucleic acid hybridization rate by polyethylene glycol," Analytical Biochemistry, vol. 152, No. 2, pp. 304-307 (Feb. 1, 1986).
Bouché et al., "The effect of spermidine on endonuclease inhibition by agarose contaminants," Analytical Biochemistry, vol. 115, No. 1, pp. 42-45 (Jul. 15, 1981).
Kuznetsova et al., "What Macromolecular Crowding Can Do to a Protein," Int. J. Mol. Sci., vol. 15, No. 12, pp. 23090-23140 (Dec. 1, 2014).
Oupicky et al., "Laterally stabilized complexes of DNA with linear reducible polycations: Strategy for triggered intracellular actication of DNA delivery vectors," Journal of the American Chemical Society, vol. 124, No. 1, pp. 8-9 (Jan. 9, 2002).
Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.
Wright et al., "Dynamic closed-loop system for focus tracking using a spatial light modulator and a deformable membrane mirror," Optics Express, vol. 14, No. 1, pp. 222-228 (Jan. 9, 2006).
Wang et al., "The method of axial drift compensation of laser differential confocal microscopy based on zero-tracking," Proc. of SPIE, vol. 9618, 96180X (2015).
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Markaki et al. "Fluorescence In Situ Hybridization Applications for Super-Resolution 3D Structured Illumination Microscopy" Methods in Microbiology, Jan. 2013.
Achim et al. "High-throughput spatial mapping of single-cell RNA-seq data to tissue of origin" Nature Biotechnology, Apr. 13, 2015.
Terry R, Porreca G, McCarthy K, Church GM. 2008. Polonator Instrument http://www.polonator.org; Wayback Machine (Aug. 7, 2008) "Open, Affordable, Sequencing . . . ".
Terry R, Porreca G, McCarthy K, Church GM. 2008. Polonator Instrument http://www.polonator.org; Wayback Machine (Aug. 7, 2008) "The Vision".
Terry R, Porreca G, McCarthy K, Church GM. 2008. Polonator Instrument http://www.polonator.org; Wayback Machine (Aug. 7, 2008) "The Polonator Ecosystem".
Terry R, Porreca G, McCarthy K, Church GM. 2008. Polonator Instrument http://www.polonator.org; Wayback Machine (Aug. 7, 2008) "Instrument Overview".
Terry R, Porreca G, McCarthy K, Church GM. 2008. Polonator Instrument http://www.polonator.org; Wayback Machine (Aug. 7, 2008) "Protocols".
Terry R, Porreca G, McCarthy K, Church GM. 2008. Polonator Instrument http://www.polonator.org; Wayback Machine (Sep. 5, 2008) "PET (Paired End-Tag) Genomic Shotgun Library Construction Protocol".
Terry R, Porreca G, McCarthy K, Church GM. 2008. Polonator Instrument http://www.polonator.org; Wayback Machine (Sep. 5, 2008) "Emulsion PCR Protocol".
Terry R, Porreca G, McCarthy K, Church GM. 2008. Polonator Instrument http://www.polonator.org; Wayback Machine (Sep. 5, 2008) "Emulsion Breaking Protocol".
Terry R, Porreca G, McCarthy K, Church GM. 2008. Polonator Instrument http://www.polonator.org; Wayback Machine (Sep. 5, 2008) "Bead Enrichment Protocol".
Terry R, Porreca G, McCarthy K, Church GM. 2008. Polonator Instrument http://www.polonator.org; Wayback Machine (Sep. 5, 2008) "Bead Capping Protocol".
Terry R, Porreca G, McCarthy K, Church GM. 2008. Polonator Instrument http://www.polonator.org; Wayback Machine (Sep. 5, 2008) "Coverslip Aminosilanation and Arraying Protocol".
Terry R, Porreca G, McCarthy K, Church GM. 2008. Polonator Instrument http://www.polonator.org; Wayback Machine (Sep. 5, 2008) "Polony Sequence by Ligation Protocol".
Terry R, Porreca G, McCarthy K, Church GM. 2008. Polonator Instrument http://www.polonator.org; Wayback Machine (Jul. 5, 2008) "Polony Sequence Protocols".
Terry R, Porreca G, McCarthy K, Church GM. 2008. Polonator Instrument http://www.polonator.org; Wayback Machine (Sep. 5, 2008) "Help Wanted".
Terry R, Porreca G, McCarthy K, Church GM. 2008. Polonator Instrument http://www.polonator.org; Wayback Machine (Aug. 7, 2008) "Software".
Terry R, Porreca G, McCarthy K, Church GM. 2008. Polonator Instrument http://www.polonator.org; Wayback Machine (Aug. 7, 2008) "Reagent Kits".
Terry R, Porreca G, McCarthy K, Church GM. 2008. Polonator Instrument http://www.polonator.org; Wayback Machine (Sep. 5, 2008) "Run Kits".
Terry R, Porreca G, McCarthy K, Church GM. 2008. Polonator Instrument http://www.polonator.org; Wayback Machine (Sep. 5, 2008) "Paired-Leg Library Kits".
Terry R, Porreca G, McCarthy K, Church GM. 2008. Polonator Instrument http://www.polonator.org; Wayback Machine (Sep. 5, 2008) "Emulsion PCR/Bead Capping Kits".
Terry R, Porreca G, McCarthy K, Church GM. 2008. Polonator Instrument http://www.polonator.org; Wayback Machine (Sep. 5, 2008) "Enrichment Kits".
Terry R, Porreca G, McCarthy K, Church GM. 2008. Polonator Instrument http://www.polonator.org; Wayback Machine (Aug. 7, 2008) "Flow Cells".
Church GM. 2006. "Genomes for all" Sci Am 294: 46-54.
De Bakker PI, Yelensky R, Pe'er I, Gabriel SB, Daly MJ, Altshuler D. 2005. "Efficiency and power in genetic association studies" Nat Genet 37: 1217-23.
Dixon AL, Liang L, Moffatt MF, Chen W, Heath S, Wong KC, Taylor J, Burnett E, Gut I, Farrall M, Lathrop GM, Abecasis GR, Cookson WO. 2007. "A genome-wide association study of global gene expression" Nat Genet 39: 1202-7.
Emilsson V, Thorleifsson G, Zhang B, Leonardson AS, Zink F, Zhu J, Carlson S, Helgason A, Walters GB, Gunnarsdottir S, Mouy M, Steinthorsdottir V, Eiriksdottir GH, Bjornsdottir G, Reynisdottir I, Gudbjartsson D, Helgadottir A, Jonasdottir A, Jonasdottir A, Styrkarsdottir U, Gretarsdottir S, Magnusson KP, Stefansson H, Fossdal R, Kristjansson K, Gislason HG, Stefansson T, Leifsson BG, Thorsteinsdottir U, Lamb JR, Gulcher Jr, Reitman ML, Kong A, Schadt EE, Stefansson K. 2008; "Genetics of gene expression and its effect on disease" Nature 452: 423-8.
Risch N, Merikangas K. 1996. "The future of genetic studies of complex human diseases" Science 273: 1516-7.
Schadt EE, Monks SA, Drake TA, Lusis AJ, Che N, Colinayo V, Ruff TG, Milligan SB, Lamb JR, Cavet G, Linsley PS, Mao M, Stoughton RB, Friend SH. 2003. "Genetics of gene expression surveyed in maize, mouse and man" Nature 422:297-302.
Altshuler D, Daly MJ, Lander ES. 2008. "Genetic mapping in human disease" Science 322: 881-8.
Cookson W, Liang L, Abecasis G, Moffatt M, Lathrop M. 2009. "Mapping complex disease traits with global gene expression" Nat Rev Genet 10: 184-94.
International HapMap C. 2005. "A haplotype map of the human genome" Nature 437: 1299-320. PMC ID: PMC1880871.
Klein RJ. 200T "Power analysis for genome-wide association studies" BMC Genet 8: 58. PMC ID: PMC2042984.
Kwan T, Benovoy D, Dias C, Gurd S, Provencher C, Beaulieu P, Hudson TJ, Sladek R, Majewski J. 2008. "Genome-wide analysis of transcript isoform variation in humans" Nat Genet 40: 225-31.
McCarroll SA. 2008. "Extending genome-wide association studies to copy-number variation" Hum Mol Genet 17: R135-42.
Morley M, Molony CM, Weber TM, Devlin JL, Ewens KG, Spielman RS, Cheung VG. 2004. "Genetic analysis of genome-wide variation in human gene expression" Nature 430: 743-7.
Sachidanandam R, Weissman D, Schmidt SC, Kakol JM, Stein LD, Marth G, Sherry S, Mullikin JC, Mortimore BJ, Willey DL, Hunt SE, Cole CG, Coggill PC, Rice CM, Ning Z, Rogers J, Bentley DR,

(56) References Cited

OTHER PUBLICATIONS

Kwok PY, Mardis ER, Yeh RT, Schultz B, Cook L, Davenport R, Dante M, Fulton L, Hillier L, Waterston RH, McPherson JD, Gilman B, Schaffner S, Van Etten WJ, Reich D, Higgins J, Daly MJ, Blumenstiel B, Baldwin J, Stange-Thomann N, Zody MC, Linton L, Lander ES, Altshuler D, International SNPMWG. 2001. A map of human genome sequence variation containing 1.42 million single nucleotide polymorphisms. Nature 409:928-933.

Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. "Mapping the genetic architecture of gene expression in human liver" PLoS Biol 6: e107. PMC ID: PMC2365981.

Serve D, Gurd S, Ge B, Sladek R, Sinnett D, Harmsen E, Bibikova M, Chudin E, Barker DL, Dickinson T, Fan JB, Hudson TJ. 2008. "Differential allelic expression in the human genome: a robust approach to identify genetic and epigenetic cis-acting mechanisms regulating gene expression" PLoS Genet 4: e1000006. PMC ID: PMC2265535.

Ball MP, Li JB, Gao Y, Lee J, LeProust E, Park I-H, Xie B, Daley GQ, Church GM. 2009. "Targeted and whole-genome methylomics reveals gene-body signatures in human cell lines" Nat Biotechnol 27: 361-8.

Brenner S, Williams SR, Vermaas EH, Storck T, Moon K, McCollum C, Mao JI, Luo S, Kirchner JJ, Eletr S, DuBridge RB, Burcham T, Albrecht G. 2000. "In vitro cloning of complex mixtures of DNA on microbeads: physical separation of differentially expressed cDNAs" Proc Natl Acad Sci U S A 97: 1665-70. PMC ID: PMC26493.

Chiang DY, Getz G, Jaffe DB, O'Kelly MJ, Zhao X, Carter SL, Russ C, Nusbaum C, Meyerson M, Lander ES. 2009. "High-resolution mapping of copy-number alterations with massively parallel sequencing" Nat Methods 6: 99-103. PMC ID: PMC2630795.

Choy E, Yelensky R, Bonakdar S, Plenge RM, Saxena R, De Jager PL, Shaw SY, Wolfish CS, Slavik JM, Cotsapas C, Rivas M, Dermitzakis ET, Cahir-McFarland E, Kieff E, Hailer D, Daly MJ, Altshuler D. 2008. "Genetic analysis of human traits in vitro: drug response and gene expression in lymphoblastoid cell lines" PLoS Genet 4: e1000287. PMC ID: PMC2583954.

Christian AT, Pattee MS, Attix CM, Reed BE, Sorensen KJ, Tucker JD. 2001. "Detection of DNA point mutations and mRNA expression levels by rolling circle amplification in individual cells" Proc Natl Acad Sci U S A 98: 14238-43. PMC ID: PMC64666.

Church GM, Porreca GJ, Terry RC, Lares M. 2008. "High-Speed Imaging for DNA Sequencing" Biophotonics (<http://www.photonics.com/Content/ReadArticle.aspx?ArticleID=33989>).

Deng J, Shoemaker R, Xie B, Gore A, LeProust EM, Antosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylation associated with nuclear reprogramming" Nat Biotechnol 27: 353-60.

Eberwine J, Kacharmina JE, Andrews C, Miyashiro K, McIntosh T, Becker K, Barrett T, Hinkle D, Dent G, Marciano P. 2001. "mRna expression analysis of tissue sections and single cells" J Neurosci 21: 8310-4.

Kolb HC, Finn MG, B. SK. 2001. "Click Chemistry: Diverse Chemical Function from a Few Good Reactions" Angew. Chem. Int. 40: 2004-21.

Kwiatkowski M, Fredriksson S, Isaksson A, Nilsson M, Landegren U. 1999. "Inversion of in situ synthesized oligonucleotides: improved reagents for hybridization and primer extension in DNA microarrays" Nucleic Acids Res 27: 4710-4. PMC ID: PMC148770.

Li JB, Gao Y, Aach J, Zhang K, Kryukov GV, Xie B, Ahlford A, Yoon J-K, Rosenbaum AM, Wait-Zaranek A, LeProust E, Sunyaev S, Church GM. 2009. "Multiplex padlock capture and sequencing reveal human hypermutable CpG variations" Genome Res in press.

Mitra RD, Bully VL, Shendure J, Williams BR, Housman DE, Church GM. 2003. "Digital genotyping and haplotyping with polymerase colonies" Proc Natl Acad Sci U S A 100: 5926-31. PMC ID: PMC156303.

Pan X, Urban AE, Palejev D, Schulz V, Grubert F, Hu Y, Snyder M, Weissman SM. 2008. "A procedure for highly specific, sensitive, and unbiased whole-genome amplification" Proc Natl Acad Sci U S A 105: 15499-504. PMC ID: PMC2563063.

Stougaard M, Lohmann JS, Zajac M, Hamilton-Dutoit S, Koch J. 2007. "In situ detection of non-polyadenylated RNA molecules using Turtle Probes and target primed rolling circle PRINS" BMC Biotechnol 7: 69. PMC ID: PMC2203993.

Wang Z, Gerstein M, Snyder M. 2009. "RNA-Seq: a revolutionary tool for transcriptomics" Nat Rev Genet 10: 57-63.

Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci U S A 104: 16462-7. PMC ID: PMC2034218.

Zang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" (submitted to Nature Methods).

Bakal C, Aach J, Church G, Perrimon N. 2007. "Quantitative morphological signatures define local signaling networks regulating cell morphology" Science 316: 1753-6.

Bang D, Church GM. 2008. "Gene synthesis by circular assembly amplification" Nat Methods 5: 37-9.

Bell J. 2004. "Predicting disease using genomics" Nature 429: 453-6.

Eid J, Fehr A, Gray J, Luong K, Lyle J, Otto G, Peluso P, Rank D, Baybayan P, Bettman B, Bibillo A, Bjornson K, Chaudhuri B, Christians F, Cicero R, Clark S, Dalai R, Dewinter A, Dixon J, Foquet M, Gaertner A, Hardenbol P, Heiner C, Hester K, Holden D, Kearns G, Kong X, Kuse R, Lacroix Y, Lin S, Lundquist P, Ma C, Marks P, Maxham M, Murphy D, Park I, Pham T, Phillips M, Roy J, Sebra R, Shen G, Sorenson J, Tomaney A, Travers K, Trulson M, Vieceli J, Wegener J, Wu D, Yang A, Zaccarin D, Zhao P, Zhong F, Korlach J, Turner S. 2009. Real-time DNA sequencing frpm single polymerase molecules. Science 323:133-138.

Harris TD, Buzby PR, Babcock H, Beer E, Bowers J, Braslavsky I, Causey M, Colonell J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320: 106-9.

Kim JB, Porreca GJ, Song L, Greenway SC, Gorham JM, Church GM, Seidman CE, Seidman JG. 2007 "Polony multiplex analysis of gene expression (PMAGE) in mouse hypertrophic cardiomyopathy" Science 316: 1481-4.

Kurimoto K, Yabuta Y, Ohinata Y, Saitou M. 2007. "Global single-cell cDNA amplification to provide a template for representative high-density oligonucleotide microarray analysis" Nat Protoc 2: 739-52.

Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.

Meng Q, Kim DH, Bai X, Bi L, Turro NJ, Ju J. 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.

Mitra RD, Shendure J, Olejnik J, Edyta Krzymanska O, Church GM. 2003. "Fluorescent in situ sequencing on polymerase colonies" Anal Biochem 320: 55-65.

Porreca GJ, Shendure J, Church GM. 2006. "Polony DNA sequencing" Curr Protoc Mol Biol Chapter 7: Unit 7 8.

Porreca GJ, Zhang K, Li JB, Xie B, Austin D, Vassallo SL, LeProust EM, Peck BJ, Emig CJ, Dahl F, Gao Y, Church GM, Shendure J. 2007 "Multiplex amplification of large sets of human exons" Nat Methods 4: 931-6.

Shendure J, Mitra RD, Varma C, Church GM. 2004. "Advanced sequencing technologies: methods and goals" Nat Rev Genet 5: 335-44.

(56) References Cited

OTHER PUBLICATIONS

Shendure JA, Porreca GJ, Church GM. 2008. "Overview of DNA sequencing strategies" Curr Protoc Mol Biol Chapter 7: Unit 7 1.

Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.

Vigneault F, Sismour AM, Church GM. 2008"Efficient microRNA capture and bar-coding via enzymatic oligonucleotide adenylation" Nat Methods 5: 777-9.

Zhang K, Martiny AC, Reppas NB, Barry KW, Malek J, Chisholm SW, Church GM. 2006. "Sequencing genomes from single cells by polymerase cloning" Nat Biotechnol 24: 680-6.

Zhang K Zhu J, Shendure J, Porreca GJ, Aach JD, Mitra RD, Church GM. 2006. "Long-range polony haplotyping of individual human chromosome molecules" Nat Genet 38: 382-7.

Church et al.; Center for Casual Consequences of Variation (CCV) "An NHGRI Center for Excellence in Genomic Science" http://ccv.med.harvard.edu; Wayback Machine (Jul. 3, 2011).

Church et al.; Center for Casual Consequences of Variation (CCV) "Our four Specific Aims" http://ccv.med.harvard.edu/specific_aims.htm; Wayback Machine (Aug. 13, 2011).

Church; "Proposal for a Center for the determination of the Casual Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).

J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.

PI: Piezo Nano Positioning, 2008 (online), retrieved on Aug. 12, 2020, pp. 1-6 <https://www.pi-usa.us/fileadmin/user_upload/pi_us/files/product_datasheets/N725_Piezo_Focus_Positioner.pdf>.

Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.

Pihlak et al. "Rapid genome sequencing with short universal tiling probes" Nature Biotechnology, vol. 26, No. 6, Jun. 2008, pp. 676-684.

Lizardi "Next-generation sequencing-by-hybridization" Nature Biotechnology, vol. 26, No. 6, Jun. 2008, pp. 649-650.

Mignardi et al. "Fourth-generation sequencing in the cell and the clinic" Genome Medicine, 2014, 6:31.

* cited by examiner

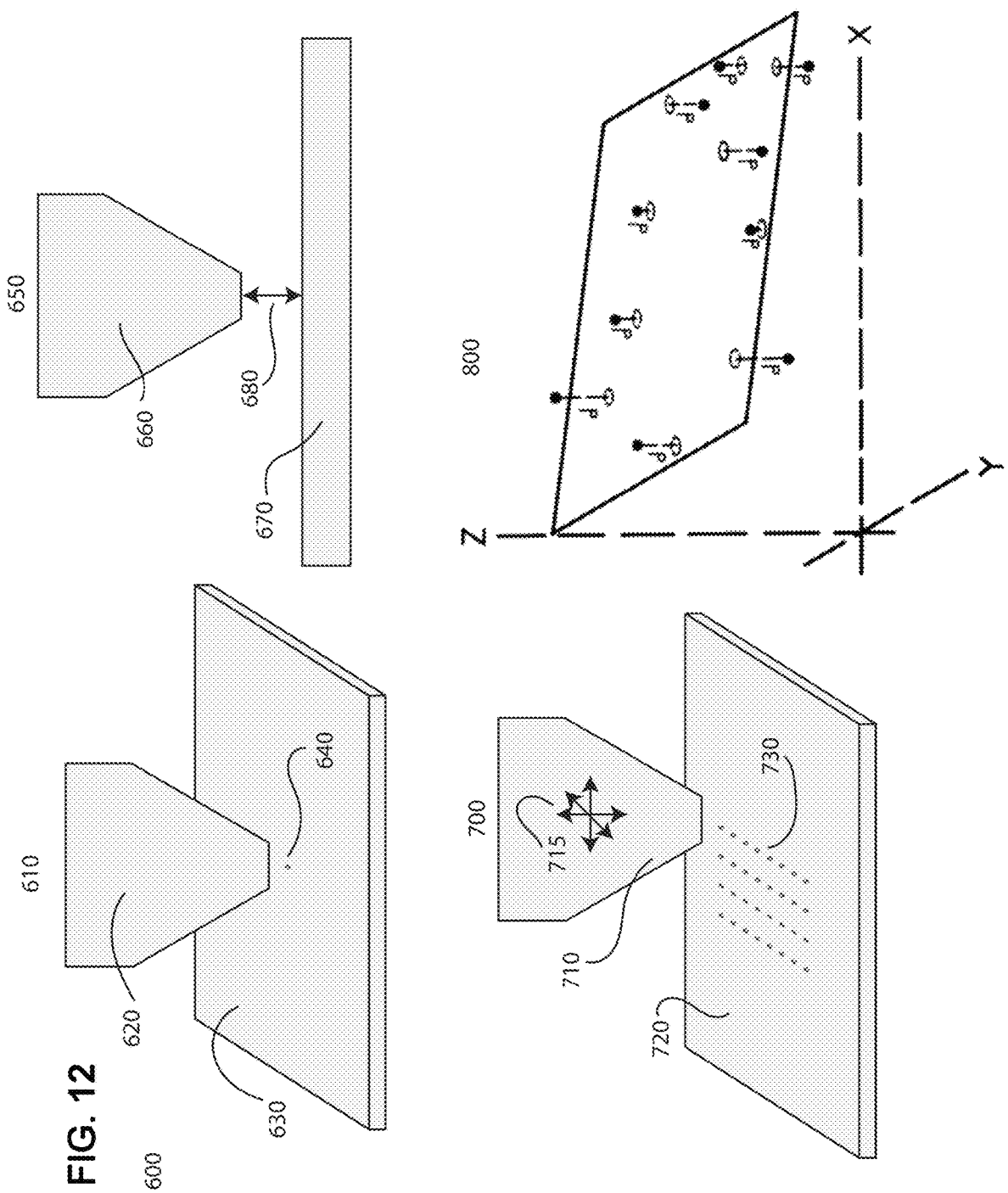

METHOD AND APPARATUS FOR VOLUMETRIC IMAGING OF A THREE-DIMENSIONAL NUCLEIC ACID CONTAINING MATRIX

RELATED APPLICATION DATA

This application is a continuation application which claims priority to U.S. patent application Ser. No. 15/969,118, filed on May 2, 2018, which is a continuation of PCT application no. PCT/US2016/060279, designating the United States and filed Nov. 3, 2016; which claims the benefit U.S. Provisional Patent Application No. 62/250,182 filed on Nov. 3, 2015 each of which is hereby incorporated herein by reference in their entirety for all purposes.

STATEMENT OF GOVERNMENT INTERESTS

This invention was made with Government support under grant number P50 HG005550 awarded by National Institutes of Health, RC2HL102815 awarded by National Institutes of Health, MH098977 awarded by National Institutes of Health, GM080177 awarded by National Institutes of Health and DGE1144152 awarded by National Science Foundation. The Government has certain rights in the invention.

FIELD OF THE INVENTION

The present invention relates to a method and apparatus for volumetric imaging of a three-dimensional matrix of nucleic acids where the nucleic acids have been amplified, detected and sequenced within the matrix.

BACKGROUND OF THE INVENTION

Since many gene products such as RNA and proteins are enriched in regions where they function, their location provides an important clue to their function. This property has been used for in situ fluorescent hybridization, immunohistochemistry and tissue-specific reporter assays in numerous areas of biological research. Most optical sequencing methods either utilize a two-dimensional solid substrate or microwells/microchambers to immobilize sequencing templates during the sequencing process in order to maintain spatial invariability for optical detection, and therefore enable reconstruction of a single nucleic acid template sequence. In both cases, optical detection of signal occurs in at most two two-dimensional planes.

SUMMARY

Embodiments of the present invention are directed to volumetric imaging of nucleic acids within a three-dimensional matrix, such as within a fixed biological specimen, and an apparatus for volumetric imaging of nucleic acids within a three-dimensional matrix, such as within a fixed biological specimen. Volumetric imaging detects fluorescence- or optically-encoded signals in three dimensions. According to one aspect, the three-dimensional positioning of a molecule within the three dimensional matrix is determined. According to certain aspects, methods are provided for imaging an arbitrary volume in a method of volumetric detection, imaging, and reconstruction. Exemplary volumetric detection methods include both methods for volumetric imaging of optical sections that utilize optical sectioning (e.g. two-dimensional acquisition of images throughout a volume), as well as those that do not utilize optical sectioning (e.g. digital holography and physical sectioning).

Aspects of the present disclosure may include in situ nucleic acid sequencing methods using a three-dimensional matrix for immobilization of nucleic acid sequencing templates during sequencing, maintaining the spatial relationships in three dimensions between sequencing templates, enabling detection and reconstruction of both sequences and three-dimensional positional information. Exemplary methods described herein are also directed to reconstruct three-dimensional biological features, such as proteins and cell membranes. Exemplary volumetric imaging approaches include those described herein and those known in the art which measure light signals, systematically or otherwise, in three-dimensional space. Accordingly, aspects of the present disclosure include a method and apparatus for volumetric imaging of in situ sequenced nucleic acids. Aspects of the present disclosure further include an automated method and apparatus for volumetric imaging of in situ sequenced nucleic acids including an in situ sequencing method or apparatus, a fluidics method or reagent delivery method or apparatus to regulate flow of reagents and deliver reagents and a volumetric imaging method or apparatus for imaging and/or detecting light signals from the in situ sequenced nucleic acids or other molecules or structures of interest. According to certain aspects, the methods and apparatus described herein are not limited to nucleic acids. Any molecule or structure within a three dimensional matrix that can be detected, for example, using detectable moieties, such as fluorescent moieties and other detectable moieties known to those of skill in the art can be the subject of the volumetric imaging methods described herein. Such molecules or structures can include DNA, RNA, proteins, biomolecules, cellular structures and the like.

Exemplary methods of making a three dimensional matrix of nucleic acid sequences, amplifying such nucleic acid sequences, sequencing such nucleic acid sequences and imaging such nucleic acid sequences are provided in PCT US2014/18580 hereby incorporated by reference in its entirety. Such methods include making a three dimensional matrix including nucleic acids covalently bound into a matrix or into or to a matrix material. The nucleic acids may be co-polymerized with the matrix material or cross-linked to the matrix material or both. According to one aspect, a plurality of nucleic acid sequences of certain length, such as DNA or RNA sequences are part of a three-dimensional copolymer. According to one aspect, nucleic acids such as DNA or RNA sequences of given length are covalently attached to a matrix material to preserve their spatial orientation in the x, y and z axes within the matrix. It is to be understood that the three dimensional matrix may include a matrix material and that the term copolymer, matrix and matrix material may be used interchangeably. Useful methods also include immobilizing naturally occurring nucleic acids within their native environment, such as within a cell or within a tissue sample. The three dimensional nucleic acid matrix can be generated in situ in a cell or tissue sample to preserve the naturally occurring nucleic acid sequence diversity (such as DNA and RNA) and spatial orientation in cells, tissues or any other complex biomaterial. According to this aspect, the location of nucleic acids and their relative position is identified as a three dimensional structure, such as within subcellular compartments, within cells, within tissues, as three dimensional nucleic acid assemblies, as three dimensional nucleic acid material, etc. The nucleic acids can be amplified and sequenced, if desired, in situ thereby providing positional information of the nucleic acids within the cell or tissue.

According to a related aspect, nucleic acids of interest or other molecules of interest, whether naturally occurring or synthetic, can be present within a three dimensional matrix material and covalently attached to the three dimensional matrix material such that the relative position of each nucleic acid is fixed, i.e. immobilized, within the three dimensional matrix material. In this manner, a three-dimensional matrix of covalently bound nucleic acids of any desired sequence is provided. Each nucleic acid has its own three dimensional coordinates within the matrix material and each nucleic acid represents information. According to one aspect, individual nucleic acids, such as DNA or RNA can be amplified and sequenced in situ, i.e., within the matrix.

According to a further aspect, the nucleic acids can be amplified to produce amplicons within the three dimensional matrix material. The amplicons can then be covalently attached to the matrix, for example, by copolymerization or cross-linking. This results in a structurally stable and chemically stable three dimensional matrix of nucleic acids. According to this aspect, the three dimensional matrix of nucleic acids allows for prolonged information storage and read-out cycles. The nucleic acid/amplicon matrix allows for high throughput sequencing of a wide ranging array of biological and non-biological samples in three dimensions.

According to certain aspects, a three dimensional nucleic acid matrix is provided where a plurality of nucleic acid molecules, such as DNA or RNA, amplicons or nucleic acid structural units are immobilized, such as by covalent bonding to the matrix, in a three dimensional space relative to one another. In this context, the nucleic acid molecules are rigidly fixed to the extent that they maintain their coordinate position within the matrix. It is to be understood that even though a nucleic acid molecule may be covalently attached to the three dimensional matrix material, the nucleic acid molecule itself may be capable of movement though bound to the matrix, such as for example, when a nucleic acid sequence is bound to the matrix at a single location on the nucleic acid.

According to one aspect, the three dimensional matrix including nucleic acids is porous. According to one aspect, the three dimensional matrix including nucleic acids is porous to the extent that reagents typically used in amplification methods can diffuse or otherwise move through the matrix to contact nucleic acids and thereby amplify nucleic acids under suitable conditions. Porosity can result from polymerization and/or crosslinking of molecules used to make the matrix material. The diffusion property within the gel matrix is largely a function of the pore size. The molecular sieve size is chosen to allow for rapid diffusion of enzymes, oligonucleotides, formamide and other buffers used for amplification and sequencing (>50-nm). The molecular sieve size is also chosen so that large DNA or RNA amplicons do not readily diffuse within the matrix (<500-nm). The porosity is controlled by changing the cross-linking density, the chain lengths and the percentage of co-polymerized branching monomers according to methods known to those of skill in the art.

According to one aspect, the three dimensional matrix material is chemically inert and thermally stable to allow for various reaction conditions and reaction temperatures. According to this aspect, the three dimensional matrix material is chemically inert and thermally stable to conditions used in amplification and sequencing methods known to those of skill in the art.

According to one aspect, the three dimensional matrix material is optically transparent. According to one aspect, the three dimensional matrix material is optically transparent to allow for three dimensional imaging techniques known to those of skill in the art.

According to one aspect, the nucleic acids are amplified to an extent to produce sufficient levels of amplicons for three dimensional imaging. For example, the nucleic acids are amplified and include a label sufficient for a high level of fluorescence compatible with three dimensional imaging.

According to one aspect, the material used to form the matrix is compatible with a wide range of biological and non-biological specimens in situ so as to avoid extracting the nucleic acid molecules away from their native environment.

According to one aspect, the matrix material may be a semi-solid medium that can be made from polyacrylamide, cellulose, alginate, polyamide, cross-linked agarose, cross-linked dextran or cross-linked polyethylene glycol. In certain aspects, the semi-solid medium has x, y and z axes, and the nucleic acids are present randomly or non-randomly within the three dimensional matrix.

In certain aspects, the semi-solid medium can be attached to a solid support such as a microscope slide or a flow cell. The solid support can be attached to the bottom surface of the semi-solid medium.

According to one aspect, an automated method and device is provided for introducing reagents into the matrix, such as for example, by using fluidics or microfluidics devices including one or more reservoirs which reagents are stored, channels or conduits to direct the reagents to the matrix and one or more pumps to force or draw the reagents from the reservoirs through the channels or conducts and to the matrix. The automated method and device may be controlled by a microprocessor and software.

BRIEF DESCRIPTION OF THE DRAWINGS

The foregoing and other features and advantages of the present invention will be more fully understood from the following detailed description of illustrative embodiments taken in conjunction with the accompanying drawings.

DETAILED DESCRIPTION

Figure 1:
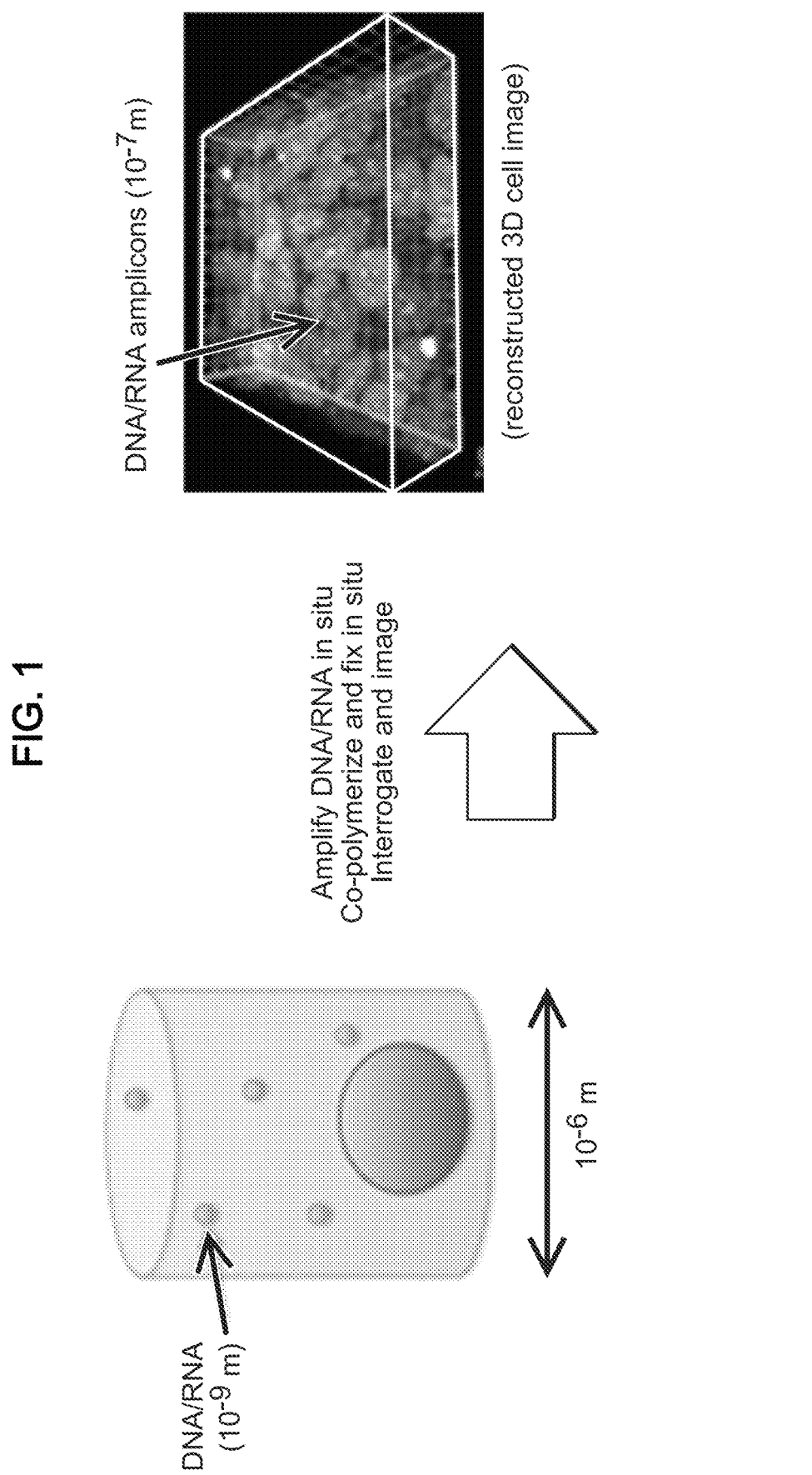
FIG. 1 depicts in schematic the process of creating a matrix of nucleic acids within cells in situ, followed by amplifying the nucleic acids, such as DNA or RNA, in situ, co-polymerizing the amplicons in situ, covalently attaching the amplicons to the matrix material, interrogating the amplicons and imaging the amplicons along with a reconstructed 3D cell image with DNA/RNA amplicons on the order of 10-7 m.

The present invention provides a method and apparatus for analysis of molecules present within a three-dimensional matrix, such as a plurality of nucleic acids within a three-dimensional matrix. According to one aspect, an automated sequencing and three-dimensional imaging device (i.e., volumetric imaging device) is provided that can measure, resolve and optionally localizing light signals in three-dimensional space to measure fluorescently- or optically-encoded nucleic-acid sequencing within a three-dimensional matrix.

According to one aspect, the nucleic acids have been amplified and sequenced using optical sequencing methods known to those of skill in the art so that the nucleic acid can be optically detected. According to one aspect, an automated sequencing and three-dimensional imaging device is provided which includes a three-dimensional imaging apparatus, apparatus for fluid exchange, apparatus for temperature control, and apparatus for computational analysis. The automated sequencing and three-dimensional imaging device uses biochemical methods to execute fluorescence- or optically-encoded nucleic acid sequencing, acquisition of image data, and optionally, data processing.

According to one aspect, a plurality of nucleic acids within a three-dimensional matrix that have been amplified and sequenced using optical sequencing methods known to those of skill in the art so that the nucleic acid can be optically detected is volumetrically imaged. According to this aspect, during detection of fluorescence- or optically-encoded nucleic acid sequencing chemistry, light emanates from a nucleic acid template molecule or multimolecular amplicon in three dimensions upon excitation. The three-dimensional distribution of emission light, called a point spread function, is created by an optical system when imaging a point source. In traditional wide-field microscopy systems, as the focal plane distance increases from the point source in Z, the image becomes less point-like. The total integrated intensity at each out-of-focus plane is the same as that at the focal plane, but in practice the intensity level drops below the sensitivity of the detector after a certain distance. The out-of-focus light is also dispersed, enabling resolution of objects in another focal plane whose intensity is greater than the out-of-focus background. The size and shape of the point spread function is determined by the optical system, especially the numerical aperture of the objective. Although wide-field microscopy can be used to image a volume in this way, additional methods achieve greater axial resolution and signal-to-noise.

Exemplary volumetric imaging approaches used in the automated sequencing and three-dimensional imaging device described herein are broadly divided into two categories: structured illumination and emission manipulation. Additional approaches include computational reconstruction and measurement of angular components of emission light. These approaches provide a systematic measurement of the intensity and wavelength of light in three-dimensional space.

According to one aspect, an automated sequencing and three-dimensional imaging device is provided which includes a three-dimensional imaging apparatus where the three-dimensional matrix is imaged using 3D Structured Illumination (3DSIM). In 3DSIM, spatially patterned light is used for excitation, and fringes in the Moiré pattern generated by interference of the illumination pattern and the sample, are used to reconstruct the source of light in three dimensions. Multiple spatial patterns are used to excite the same physical region in order to illuminate the whole field. Digital processing or analog methods are used to reconstruct the final image. See York, Andrew G., et al. "Instant super-resolution imaging in live cells and embryos via analog image processing." *Nature methods* 10.11 (2013): 1122-1126 and Gustafsson, Mats G L, et al. "Three-dimensional resolution doubling in wide-field fluorescence microscopy by structured illumination." Biophysical journal 94.12 (2008): 4957-4970 each of which are hereby incorporated by reference in their entireties.

Two-photon, or multi-photon, microscopic modalities are useful structured illumination microscopy methods. See Denk W., Strickler J., Webb W. (1990). "Two-photon laser scanning fluorescence microscopy". *Science* 248 (4951): 73-6 hereby incorporated by reference in its entirety. Two-photon microscopy is a type of microscopy that enables imaging deep within a sample by using two photons per excitation event. These systems typically use long-wavelength light for excitation, which penetrates more effectively into tissue due to reduced scattering. The use of two-photon excitation also reduces background signal as single-photon absorption provides insufficient energy to excite emission by the fluorophore. Two-photon microscopy can also utilize larger or more efficient optical and sensor configurations to detect the emission, as the localization of excitation over time is known to the imaging system during scanning. Other benefits to this modality include reduced photodamage to the sample.

According to one aspect, an automated sequencing and three-dimensional imaging device is provided which includes a three-dimensional imaging apparatus where the three-dimensional matrix is imaged using a planar illumination method such as selective planar illumination microscopy (SPIM) or light sheet microscopy (LSM). In SPIM, optical detecting moieties are excited selectively in each plane in a third dimension while a two-dimensional image is acquired in the plane orthogonal to the illumination axis, providing effective separation over imaging time/frames between objects distributed in the third dimension. See Huisken, Jan, et al. "Optical sectioning deep inside live embryos by selective plane illumination microscopy." *Science* 305.5686 (2004): 1007-1009 hereby incorporated by reference in its entirety. Systematic sequential imaging of planes provides for volumetric measurement. The planar illumination light may be generated using any number of approaches such as Gaussian and Bessel beam shaping.

According to one aspect, an automated sequencing and three-dimensional imaging device is provided which includes a three-dimensional imaging apparatus where the three-dimensional matrix is imaged using emission manipulation, such as confocal microscopy where one or more pinholes are positioned at the confocal plane of the lens, blocking out-of-focus light from reaching the detector. The focal plane of the lens is systematically shifted through the third dimension, enabling volumetric imaging. See Wilson, Tony. "Confocal microscopy." *Academic Press: London, etc* 426 (1990): 1-64 hereby incorporated by reference in its entirety.

According to one aspect, an automated sequencing and three-dimensional imaging device is provided which includes a confocal imaging or microscopy modality. According to a certain aspect, the confocal imaging or microscopy modality is a scanning laser confocal modality. According to another aspect, the confocal modality is a spinning disk confocal modality. The spinning disk may be a Nipkow disk. According to another aspect, the confocal microscopy modality is a parallel beam scanning laser modality, wherein two or more pinholes are scanned across the sample, such as by using a mirror galvanometer. The confocal modality may comprise one or more microlens arrays, such as for focusing excitation light onto the pinhole array.

According to one aspect, an automated sequencing and three-dimensional imaging device is provided which includes a three-dimensional imaging apparatus where the three-dimensional matrix is imaged using a parallel confocal method including aperture correlation. See Wilson, Tony, et al. "Confocal microscopy by aperture correlation." *Optics letters* 21.23 (1996): 1879-1881 hereby incorporated by reference in its entirety.

According to one aspect, an automated sequencing and three-dimensional imaging device is provided which includes a three-dimensional imaging apparatus where the three-dimensional matrix is imaged using a microlens array for volumetric imaging, known as light field microscopy. See, Broxton et al. (2013) "Wave Optics Theory and 3-D Deconvolution for the Light Field Microscope" *Stanford Computer Graphics Laboratory Technical Report* 2013-1 hereby incorporated by reference in its entirety. According to this aspect, a microlens array between the main lens and the detector pass light, which would otherwise focus at an intermediate plane, onto the light field for detection. 3D reconstruction algorithms are applied to generate a volumetric image.

According to one aspect, an automated sequencing and three-dimensional imaging device is provided which includes a three-dimensional imaging apparatus where the three-dimensional matrix is imaged using a method of volumetric reconstruction from slices. According to this aspect of imaging a volume of arbitrary dimension, a specimen may be sectioned into segments of arbitrary dimension for the purpose of imaging. The original volume is reconstructed using information about the relative position of each segment imaged with respect to the original volume. This process is typically referred to as "acquiring serial sections," and is used due to limitations in depth of scanning of volumetric imaging modalities, as well as by limitations of manipulating and labeling thick samples, where diffusion may limit penetration of reagents deep into specimens. In extraordinary cases, the sections may be thinner than the diffraction limit of light, enabling resolution in the axis of sectioning beyond what is achievable by the diffraction limit of light. According to the 3D volumetric reconstruction from serial sections method described herein, the sample is sectioned either before or after creation of the 3D sequencing library, but specifically in such a way that the spatial relationship between sections is preserved. For example, each section is placed in a separate well of a flowcell and given a unique identification. During sectioning, the samples are attached onto a solid support substrate, particularly by creation of covalent cross-links between the sample matrix and the solid substrate or by creation of a new encapsulating structural matrix. According to one aspect, the section is transferred onto functionalized glass and covalent chemical cross-links are formed between the glass and the 3D matrix of the sample. According to one aspect, the section is transferred onto functionalized glass and a new supporting matrix, which is covalently linked to the glass surface, is formed to encapsulate the sample and provide structural support. For example, a 4% 1:19 acrylamide:bis gel is formed around and through a section of a biological sample as the primary 3D matrix for FISSEQ; or a pre-existing FISSEQ gel (including those formed using a polyacrylamide matrix as the primary 3D matrix) is sectioned and encased in a secondary 3D stabilizing matrix.

According to one aspect, an automated sequencing and three-dimensional imaging device is provided which includes a three-dimensional imaging apparatus where the three-dimensional matrix is imaged using deconvolution microscopy including computational algorithmic methods of processing digital image data so as to remove the effect of the optical components of the microscope. See Biggs, David S C. "3D deconvolution microscopy." *Current Protocols in Cytometry* (2010): 12-19 hereby incorporated by reference in its entirety. Because optical microscopy detects point sources of light as a point spread function that exists in three dimensions, deconvolution methods described herein reassign out of focus light to the point source, often using models or measurements of the point spread function of the optical system. This can serve to effectively increase resolution in three dimensions.

According to one aspect, an automated sequencing and three-dimensional imaging device is provided which includes a three-dimensional imaging apparatus where the three-dimensional matrix is imaged using aberration-corrected multifocus microscopy to simultaneously capture images from multiple sample planes, using Diffractive Fourier optics to create an instant array of focal of 2D wide-field images, recorded simultaneously in one or more camera frames. See Abrahamsson, Sara, et al. "Fast multicolor 3D imaging using aberration-corrected multifocus microscopy." *Nature methods* 10.1 (2013): 60-63 hereby incorporated by reference in its entirety. As with microlens array microscopy, the entire imaging volume is recorded without mechanical movement of parts.

According to one aspect, an automated sequencing and three-dimensional imaging device is provided which includes a three-dimensional imaging apparatus where the three-dimensional matrix is imaged using digital holographic microscopy. According to this aspect, digital holographic microscopy does not record a projected image, but rather records the light wave front information as a hologram. See Manoharan "Digital Holographic Microscopy for 3D Imaging of Complex Fluids and Biological Systems" hereby incorporated by reference in its entirety. The amplitude and phase of light is measured using digital sensors. The hologram contains all information needed for reconstruction of the volume. If the object wave front is measured from multiple angles, all optical characteristics of the object may be fully characterized. Because there is no image-forming lens, reconstruction algorithms that model the optical system will reconstruct the volume without aberration.

According to one aspect, the automated sequencing and three-dimensional imaging device described herein can carry out one or more volumetric imaging methods, such as by including one or more volumetric imaging apparatuses to carry out one or more volumetric imaging methods. A combination of volumetric imaging methods as described herein may be used to further enhance resolution, imaging speed, light efficiency, or gain additional benefits. For example, SIM and confocal microscopy principles have been combined into multifocal SIM (mSIM). See York, Andrew G., et al. "Resolution doubling in live, multicellular organisms via multifocal structured illumination microscopy." *Nature methods* 9.7 (2012): 749-754 hereby incorporated by reference in its entirety. Also, volumetric reconstruction of slices may be combined with other methods, such as confocal microscopy, since confocal microscopy has a depth limit of hundreds of microns, while it is desirable to sequence within three-dimensional matrices of arbitrary dimensions.

According to one aspect, the automated sequencing and three-dimensional imaging device described herein comprises an imaging modality with one image sensor. According to another aspect, the automated sequencing and three-dimensional imaging device described herein comprises an imaging modality with two or more image sensors. According to one aspect, the automated sequencing and three-dimensional imaging device described herein comprises an imaging modality with four image sensors. According to one aspect, the image sensor is a photon multiplier tube (PMT). According to another aspect, the image sensor is a charge-coupled device (CCD). According to a separate aspect, the image sensor is a Complementary metal-oxide-semiconductor (CMOS). According to one aspect, the image sensor is cooled by an integrated air or liquid cooling apparatus, such as for the purpose of reducing electrical noise or to stabilize the thermal operating conditions of the sensor. Further according to this aspect, a liquid cooling apparatus may provide for cooling with reduced vibration relative to active air cooling, such as by a fan. The cooling apparatus or unit may use a heat sink in conjunction with a fan to dissipate heat produced during temperature changes. The heating or cooling apparatus or unit may use a radiator and liquid cooling/circulating system to dissipate heat produced during temperature changes. The heating or cooling apparatus or unit may use temperature sensors or thermistors to provide temperature feedback to a control system, which may be a microcontroller or built-to-task electronic circuit.

According to one aspect, the automated sequencing and three-dimensional imaging device described herein comprises a color multiplexer for detection of one or more distinct colors of light. The light emitted from one or more fluorescent emitters is detected by a detector. In certain aspects, the detector is configured to detect photons of light with certain wavelengths. According to another aspect, the emission light is filtered such that only photons of certain wavelengths are detected by a photon detector. Further according to another aspect, the device contains one or more emission filters, excitation filters, and/or dichroics for directing certain wavelengths of light within the optical system. Further according to one aspect, the device contains one or more acousto-optical tunable filter(s) (AOTF) for directing certain wavelengths of light to a certain detector or detectors. According to one aspect, colors of light signals are detected in serial. According to another aspect, two or more distinguishable colors of light are detected in parallel by one or more sensors.

According to one aspect, the automated sequencing and three-dimensional imaging device described herein is used to detect two or more colors of light in serial or parallel. According to one aspect, the colors of light being detected are spaced along the electromagnetic spectrum to facilitate discrimination between the colors. According to certain aspects, the fluorescence signals are spaced along the electromagnetic spectrum by emission wavelength to facilitate specific detection of certain fluorescent moieties. According to certain aspects, the fluorescence signals are spaced along the electromagnetic spectrum by excitation wavelength to facilitate specific excitation of certain fluorescent moieties. According to one exemplary aspect, the colors of emission light are distributed around about 510 nm, 570 nm, 620 nm, and/or 680 nm. According to another exemplary aspect, the colors of excitation light are distributed around about 480 nm, 530 nm, 590 nm, and/or 640 nm.

According to one aspect, the automated sequencing and three-dimensional imaging device described herein comprises one or more sources of light. According to one aspect, the light source is used for the purpose of exciting fluorescence emission by the sample. According to another aspect, the light source is used for the purpose of detecting absorbance, Raman scattering, or other modalities of interaction between the light and the sample. According to a certain aspect, the light source is comprised of one or more light emitting diodes (LED).

According to another aspect, the light source is comprised of one or more lasers. According to another aspect, the light source is comprised of one or more lamps, such as a mercury or metal halide lamp. According to a certain aspect, the light source is coupled to the device by free space optics, wherein the light is propagated through gas or vacuum from the source to the optical system of the device. According to another aspect, the light source is coupled to the device by a fiber optic or liquid light guide. According to an exemplary aspect, the light is transmitted in its entirety or in part along a fiber optic with a square core. Further according to this aspect, the square core is paired with a square aperture or a square field stop. Further according to this aspect, the dimensions of the square core and/or square aperture may be designed to match the dimensions of the image sensor within the optical system. According to certain aspects, multiple fibers are fused as a mechanism of combining multiple colors of light into a single fiber. According to certain aspects, multiple fibers are optically combined as a mechanism of combining multiple colors of light into a single fiber. According to certain aspects, the excitation light is passed through a shutter to control the propagation of the light into or through the optical system. According to one aspect, an acousto-optical tunable filter (AOTF) is used to control the propagation of the light into or through the optical system. According to certain aspects, the propagation of the excitation light into or through the optical system is mechanically, electrically, or electromechanically coupled with a controller system for the purpose of synchronizing one or more events within the device.

According to one aspect, the sample to be analyzed by the automated sequencing and three-dimensional imaging device described herein is a three dimensional matrix including a plurality of nucleic acids bound thereto. According to one aspect, the matrix is a three dimensional nucleic acid-containing polymer. The nucleic acids may be naturally occurring nucleic acids or non-naturally occurring nucleic acids, such as nucleic acids that have been made using synthetic methods. The nucleic acids in the three dimensional matrix may be ordered or unordered. The nucleic acids in the three dimensional matrix may be present in their natural spatial relationship within a cell, tissue or organism. The nucleic acids in the three dimensional matrix may be present in rows and columns within the three dimensional matrix such as with a regular or repeating array.

According to one aspect, the nucleic acids are modified to incorporate a functional moiety for attachment to the matrix.

The functional moiety can be covalently cross-linked, copolymerize with or otherwise non-covalently bound to the matrix. The functional moiety can react with a cross-linker. The functional moiety can be part of a ligand-ligand binding pair. dNTP or dUTP can be modified with the functional group, so that the function moiety is introduced into the DNA during amplification. A suitable exemplary functional moiety includes an amine, acrydite, alkyne, biotin, azide, and thiol. In the case of crosslinking, the functional moiety is cross-linked to modified dNTP or dUTP or both. Suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix. Suitable exemplary spacer moieties include polyethylene glycol, carbon spacers, photo-cleavable spacers and other spacers known to those of skill in the art and the like.

According to one aspect, a matrix-forming material is contacted to a plurality of nucleic acids spatially arrange in three-dimensions relative to one another.

Matrix forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art.

According to one aspect, a matrix-forming material can be introduced into a cell. The cells are fixed with formaldehyde and then immersed in ethanol to disrupt the lipid membrane. The matrix forming reagents are added to the sample and are allowed to permeate throughout the cell. A polymerization inducing catalyst, UV or functional cross-linkers are then added to allow the formation of a gel matrix. The unincorporated material is washed out and any remaining functionally reactive group is quenched. Exemplary cells include any cell, human or otherwise, including diseased cells or healthy cells. Certain cells include human cells, non-human cells, human stem cells, mouse stem cells, primary cell lines, immortalized cell lines, primary and immortalized fibroblasts, HeLa cells and neurons.

According to one aspect, a matrix-forming material can be used to encapsulate a biological sample, such as a tissue sample. The formalin-fixed embedded tissues on glass slides are incubated with xylene and washed using ethanol to remove the embedding wax. They are then treated with Proteinase K to permeabilized the tissue. A polymerization inducing catalyst, UV or functional cross-linkers are then added to allow the formation of a gel matrix. The unincorporated material is washed out and any remaining functionally reactive group is quenched.

Exemplary tissue samples include any tissue samples of interest whether human or non-human. Such tissue samples include those from skin tissue, muscle tissue, bone tissue, organ tissue and the like. Exemplary tissues include human and mouse brain tissue sections, embryo sections, tissue array sections, and whole insect and worm embryos.

The matrix-forming material forms a three dimensional matrix including the plurality of nucleic acids. According to one aspect, the matrix-forming material forms a three dimensional matrix including the plurality of nucleic acids while maintaining the spatial relationship of the nucleic acids. In this aspect, the plurality of nucleic acids is immobilized within the matrix material. The plurality of nucleic acids may be immobilized within the matrix material by copolymerization of the nucleic acids with the matrix-forming material. The plurality of nucleic acids may also be immobilized within the matrix material by crosslinking of the nucleic acids to the matrix material or otherwise crosslinking with the matrix-forming material. The plurality of nucleic acids may also be immobilized within the matrix by covalent attachment or through ligand-protein interaction to the matrix.

According to one aspect, the matrix is porous thereby allowing the introduction of reagents into the matrix at the site of a nucleic acid for amplification of the nucleic acid. A porous matrix may be made according to methods known to those of skill in the art. In one example, a polyacrylamide gel matrix is co-polymerized with acrydite-modified streptavidin monomers and biotinylated DNA molecules, using a suitable acrylamide:bis-acrylamide ratio to control the cross-linking density. Additional control over the molecular sieve size and density is achieved by adding additional cross-linkers such as functionalized polyethylene glycols. According to one aspect, the nucleic acids, which may represent bits of information, are readily accessed by oligonucleotides, such as labeled oligonucleotide probes, primers, enzymes and other reagents with rapid kinetics.

According to one aspect, the matrix is sufficiently optically transparent or otherwise has optical properties suitable for standard Next Generation sequencing chemistries and deep three dimensional imaging for high throughput information readout. The Next Generation sequencing chemistries that utilize fluorescence imaging include ABI SoLiD (Life Technologies), in which a sequencing primer on a template is ligated to a library of fluorescently labeled oligonucleotides with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The workflow is achieved using an automated fluidics and imaging device (i.e. SoLiD 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (HiSeq, Illumia).

According to certain aspects, the plurality of nucleic acids may be amplified to produce amplicons by methods known to those of skill in the art. The amplicons may be immobilized within the matrix generally at the location of the nucleic acid being amplified, thereby creating a localized colony of amplicons. The amplicons may be immobilized within the matrix by steric factors. The amplicons may also be immobilized within the matrix by covalent or noncovalent bonding. In this manner, the amplicons may be considered to be attached to the matrix. By being immobilized to the matrix, such as by covalent bonding or crosslinking, the size and spatial relationship of the original amplicons is maintained. By being immobilized to the matrix, such as by covalent bonding or crosslinking, the amplicons are resistant to movement or unraveling under mechanical stress.

According to one aspect, the amplicons, such as DNA amplicons, are then copolymerized and/or covalently attached to the surrounding matrix thereby preserving their spatial relationship and any information inherent thereto. For example, if the amplicons are those generated from DNA or RNA within a cell embedded in the matrix, the amplicons can also be functionalized to form covalent attachment to the matrix preserving their spatial information within the cell thereby providing a subcellular localization distribution pattern.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994, incorporated herein by reference in its entirety for all purposes.

As used herein, the term "nucleic acid" includes the term "oligonucleotide" or "polynucleotide" which includes a plurality of nucleotides. The term "nucleic acid" is intended to include naturally occurring nucleic acids and synthetic nucleic acids. The term "nucleic acid" is intended to include single stranded nucleic acids and double stranded nucleic acids. The term "nucleic acid" is intended to include DNA and RNA, whether single stranded or double stranded. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide.

Oligonucleotides and/or polynucleotides may be isolated from natural sources or purchased from commercial sources. Oligonucleotide and/or polynucleotide sequences may be prepared by any suitable method, e.g., the phosphoramidite method described by Beaucage and Carruthers ((1981) Tetrahedron Lett. 22: 1859) or the triester method according to Matteucci et al. (1981) J. Am. Chem. Soc. 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain embodiments of the invention oligonucleotides and/or polynucleotides may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; incorporated herein by reference in their entirety for all purposes.

Nucleic acids may be obtained from libraries, e.g., genomic libraries, cDNA libraries and the like. Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233, incorporated herein by reference in their entirety for all purposes.

In certain embodiments, nucleic acids are those found naturally in a biological sample, such as a cell or tissue.

In still other aspects, a matrix is used in conjunction with a solid support. For example the matrix can be polymerized in such a way that one surface of the matrix is attached to a solid support (e.g., a glass surface), while the other surface of the matrix is exposed or sandwiched between two solid supports. According to one aspect, the matrix can be contained within a container.

Solid supports of the invention may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

Embodiments of the present invention are further directed to the amplification of nucleic acid sequences within the matrix, i.e. in situ, within the matrix. Methods of amplifying nucleic acids include rolling circle amplification in situ. In certain aspects, methods of amplifying nucleic acids involves the use of PCR, such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. U.S.A. 91:360-364; incorporated herein by reference in their entirety for all purposes). Alternative amplification methods include: self-sustained sequence replication (Guatelli et al. (1990) Proc. Natl. Acad. Sci. USA 87:1874, incorporated herein by reference in its entirety for all purposes), transcriptional amplification system (Kwoh et al. (1989) Proc. Natl. Acad. Sci. US. 86:1173, incorporated herein by reference in its entirety for all purposes), Q-Beta Replicase (Lizardi et al. (1988) BioTechnology 6:1197, incorporated herein by reference in its entirety for all purposes), recursive PCR (Jaffe et al. (2000) J. Biol. Chem. 275:2619; and Williams et al. (2002) J. Biol. Chem. 277:7790; incorporated herein by reference in their entirety for all purposes) or any other nucleic acid amplification method using techniques well known to those of skill in the art. A variety of amplification methods are described in U.S. Pat. Nos. 6,391,544, 6,365,375, 6,294,323, 6,261,797, 6,124,090 and 5,612,199, incorporated herein by reference in their entirety for all purposes. Embodiments of the present invention are directed to methods of amplifying nucleic acids in situ within the matrix by contacting the nucleic acids within the matrix with reagents, such as primers and nucleotides, and under suitable reaction conditions sufficient to amplify the nucleic acids. According to one aspect, the matrix is porous to allow migration of reagents into the matrix to contact the nucleic acids.

In accordance with certain examples, methods of sequencing a nucleic acid in situ within a matrix are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use with the matrix in which the nucleic acids are present. Reversible termination methods use step-wise sequencing-by-synthesis biochemistry that coupled with reversible termination and removable fluorescence (Shendure et al. supra and U.S. Pat. Nos. 5,750,341 and 6,306,597, incorporated herein by reference. FISSEQ is a method whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, incorporated herein by reference in its entirety for all purposes. Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363, incorporated herein by reference in its entirety for all purposes. MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) Nat. Biotech. 18:630, incorporated herein by reference in its entirety for all purposes.

According to certain aspects, the nucleic acids within the matrix can be interrogated using methods known to those of skill in the art including fluorescently labeled oligonucleotide/DNA/RNA hybridization, primer extension with labeled ddNTP, sequencing by ligation and sequencing by synthesis. Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets.

FIG. 1 depicts in schematic the process of creating a matrix of nucleic acids within cells in situ, followed by amplifying the nucleic acids, such as DNA or RNA, in situ, co-polymerizing the amplicons in situ, covalently attaching the amplicons to the matrix material, interrogating the amplicons and imaging the amplicons along with a reconstructed 3D cell image with DNA/RNA amplicons on the order of 10-7 m. According to certain aspects, FISSEQ methods and materials useful in the practice of the methods described herein are provided in Lee et al., Nature Protocols, vol. 10, No. 3 (2015) pp. 442-458, Lee et al., Science 343, 1360-1363 (2014) and Supplementary Materials published 27 Feb. 2014 on Science Express DOI: 10.1126/scienmce.1250212 each of which are hereby incorporated by reference in its entirety.

The automated sequencing and three-dimensional imaging device may be used for detecting optical signals distributed in three dimensions. The automated sequencing and three-dimensional imaging device may be used for detecting optical signals by fluorescence microscopy. According to certain aspects, the fluorescence is generated by fluorescent dyes or fluorophores, such as cyanine. According to certain aspects, the fluorescence is generated by quantum dots or other types of nanoscale semiconductors. According to certain aspects, the fluorescence is generated by fluorescent proteins, such as GFP. The automated sequencing and three-dimensional imaging device may be used for detecting optical signals of autofluorescence, chemiluminescence, or non-fluorescent optical signals such as light absorption properties of a sample (e.g., color) or light scattering properties of a sample, e.g. Raman spectroscopy and CARS, coherent anti-Stokes Raman spectroscopy.

According to one aspect, an automated sequencing and three-dimensional imaging device is provided which uses volumetric three dimensional imaging modalities to image a three dimensional nucleic acid matrix. The optical configuration may be upright, inverted, side-view, dual-view, multi-view, or have any other orientation to enable measurement of light signals in three dimensions. The device includes hardware and software functionally assembled to enact a protocol of chemical manipulation (i.e., nucleic acid sequencing) and imaging of the three dimensional nucleic acid containing matrix which is contained within a suitable vessel or stage. The device may be referred to as a fluidic sequencing microscope to the extent that it includes hardware and software to automate sequencing and hardware and software for volumetric imaging.

The three-dimensional sequencing substrate may be contained within a sample holder such as an enclosed flow cell, or be fully or partially exposed in an open well format. An enclosed flowcell may be taken to mean any solid or semi-solid substrate with an optically clear region for imaging and a channel in which laminar flow may be established for the purposes of liquid exchange. The flowcell may have one more more inlets or outlets or ports for the purposes of liquid exchange. These physical interfaces may be statically or dynamically coupled to a fluidics system and may include wells or other reservoirs to store excess or reserve fluidics to facilitate dispensing or extraction regimes. The sample holder may be designed with additional physical features intended to interface or cooperate with fluidics systems, optical systems, or physical retention systems.

The device may include a stage for retaining the sample holder. The stage may be positioned using high-precision motion control systems, such as linear servo motors with optical encoders. Optical encoder systems may be furnished in either absolute or relative formats. In the case where the motor controller reads one or more relative encoders, homing routines may be implemented relative to limit sensors and/or physical limits to provide repeatable axis positioning. Software limits may be dynamically imposed to prevent samples or sample holders (i.e., flowcells) from colliding or interfering with other physical aspects of the device. Motor drivers responsible for the motor control may interface, over a standard communications protocol (e.g., RS-323, TCP/IP, UDP, etc), with other aspects of device software and hardware for the purposes of multi-axis, coordinated routines.

The stage may include physical mechanisms for positioning and retaining sample holders, such as slots with retention mechanisms (e.g., leaf springs or magnets) that reproducibly position sample holders/samples for interaction with fluidics and/or optical systems. The stage may include a physical means of coupling fluidic apparatuses to sample holders and/or samples. Stage components may be selected to minimize the tendency for thermal changes to introduce physical deformations or translations to the sample or sample holder. Stage components may be selected to minimize chemical reactivity with fluidics used during chemistry protocols.

According to certain aspects, the device may include a mechanism for sample holder tracking, such as by reference IDs, barcodes, RFID tags, or inclusion of other trackable labels in the sample holder. The trackable label may be automatically detected by the device, such as by detection of RFID or optical sensor for detecting a barcode, or the trackable label may be input into a computer software system by a user. One or more types of sample holders may vary in physical organization of the samples, reagent input/output, imaging interface, and other aspects of the sample holder. The sample holder tracking may further comprise a mechanism for indicating to the device controller software the configuration of the sample holder, such as by referencing an index in a database of sample holder configurations. According to other aspects, the device may contain a mechanism for automatically configuring the sample holder configuration, such as by use of RADAR/LIDAR, including RADAR/LIDAR on-a-chip systems, or by machine vision, wherein physical aspects of the sample holder are automatically detected by the system, parsed, and used to configure the device interface with the sample holder. According to other aspects, the device may utilize reference diagrams or fixtures for the purpose of configuring the device interface with the sample holder, such as a fixture for determining a physical offset for a feature of the sample holder.

According to certain aspects, the device also comprises a software interface, such as a command line interface (CLI) or graphical user interface (GUI) for configuring a sample holder definition or otherwise configuring the interface between the device and the sample holder. The device may automatically scan the imaging region of a sample holder for the purpose of generating an overview scan of the image area within the sample holder. According to one aspect, the overview scan is presented to the user via a GUI for the purpose of selecting regions of the sample for sequencing and/or imaging. According to another aspect, the device contains software programs for automatically determining the appropriate regions of the sample for sequencing and/or imaging, such as by calculation of a metric such as fluorescence intensity or entropy. The device may further comprise a computer vision system or machine learning mechanism for feature recognition of the sample holder or components thereof.

The stage may include a heating or cooling apparatus where the stage may be heated or cooled (such as through thermoelectric cooling using Peltier elements), such as according to a programmed time and temperature, such as is useful with thermo-cycling for applications such as nucleic acid hybridization, amplification and sequencing. The heating or cooling apparatus or heating or cooling unit may be capable of rapid temperature cycling. The heating or cooling apparatus or unit may use a heat sink in conjunction with a fan to dissipate heat produced during temperature changes. The heating or cooling apparatus or unit may use a radiator and liquid cooling/circulating system to dissipate heat produced during temperature changes. The heating or cooling apparatus or unit may use temperature sensors or thermistors as a means of providing temperature feedback to a control system, which may be a microcontroller or other electronic circuit.

The device may include a fluidics dispenser or fluidics unit where programmed volumes of liquid reagents are dispensed to sample holders on the stage, such as to wells or flow cells on the stage, and to the three-dimensional nucleic acid containing matrix. The fluidics dispenser or unit may include temperature control (such as through thermoelectric cooling using Peltier elements) to store reagents at a consistent temperature, and may implement either liquid or water cooling as a means of heat dissipation. A pump, such as a syringe pump, may be used to deliver fluid reagents through the fluidics dispenser. According to certain aspects, the fluidics and pressure-based fluidic dispense may be driven by the pressure differential between the inside and outside of a liquid container. For example, a pressurized bottle may be connected to an electrically actuated valve, as by a piece of tubing, such that when the valve is opened, fluid is driven through the tubing and through the valve onto a sample in an open well or into a closed flowcell. In certain aspects, two or more reagents may be dispensed to a sample holder from the same valve. These reagents may be selected upstream of the valve by means of another valve (e.g., a rotary valve) or other physical means. In other aspects, valves may be addressable by two selectable lines, such that one line may deliver water or another liquid meant to flush or otherwise clean the valve in between dispenses. A reservoir or absorbent material may be statically or dynamically positioned beneath the valve to collect rinse solution or reagent during priming and cleaning operations.

In certain implementations, the exchange of liquids in a closed flowcell may take place in an entirely closed-loop system, where tubing is connected to the flowcell in a fixed manner and a system of valves and pumps (or other pressure generating devices) controls the movement and selection of reagents delivered to the flowcell. Closed flowcells may be designed to allow for non-contact reagent dispensing into wells external to the sample channel. Such wells may be designed to hold a volume appropriate to partially or fully displace the volume of the sample-containing channel. The movement of dispensed reagent into the flowcell may then be driven by positive pressure exerted on the wells, or by negative pressure exerted on outlets at the opposite end of the sample channel. The interface between the suction-generating device and the flowcell may be transient or fixed, and may be created or adjusted by motion axes such as those driven by stepper motors, servo motors or solenoids. The interface may be further defined by the presence of suction cup devices designed to create and maintain a consistent seal while minimally perturbing the physical positioning of the sample.

In other aspects, sample holders with open well(s) may be designed with features to accommodate reagent dispensing and extraction to minimize sample perturbations, such as by including channels, slots, or other physical areas designed to sequester higher levels of liquid flow from the sample. The open well(s) may additionally have chamfered or otherwise tapered sides to accommodate the specific shape of optical system interfaces, such as by matching the side profile of an optical objective.

According to a certain implementation of the pressure-driven fluidics block, multiple distinct tubes of reagent sit inside a pressurized container, each connected to its own valve, such that when any one or more valves are actuated fluid is driven from the tube through the valve onto the sample. The valves may be of one or more general types, including but not limited to solenoid valves, rotary valves and microfluidic valves. The valves may be select to maximize precision and/or minimize dead volume. According to certain aspects, the valve bodies may be designed in such a way as to place the actuating mechanism as close to the orifice as possible, to minimize problems associated with reagent drying and/or clogging. The valves may have upstream filters, screens, or other means of preventing non-liquid materials from clogging or otherwise interfering with the valves' operation. The amount of reagent dispensed using such a pressure-driven system is determined based on the valve internal diameter, liquid viscosity, pressure differential, and time of valve actuation, and can be determined empirically and used to configure a software controller such that a desired volume is converted into a length of time (given a particular hardware configuration with particular liquid viscosity, valve internal diameter, and pressurization) during which the valve is opened or actuated. According to certain aspects, the reagent containers may be individually or collectively pressurized. The pressurization medium is ideally an inert gas such as argon. The fluidic systems may combine pump-driven and pressure-driven fluidic components. The device may include a mixer for mixing programmed volumes of liquid reagents. The aspiration system described herein is used to remove fluid from a flow cell by applying a suction force to the liquid using a pump or vacuum source. Pressure-based dispense may also be used to exchange fluids during sequencing by introducing a new reagent under pressure as above to displace the existing fluid through a channel. Pressure based dispense may be used alongside aspiration to exchange liquid in a flow cell.

According to one aspect, the device may contain a reservoir for containing bulk reagents, or reagents with larger volume. According to one such aspect, the bulk reagent reservoir may contain one or more pressurized containers within an enclosing container. According to another such aspect, the bulk reagent reservoir may contain one or more containers within a pressurized enclosing container. According to one aspect, the bulk reagent reservoir is temperature controlled, such as through thermoelectric cooling using Peltier elements, for the purpose of extending the life of and activity of one or more reagents. The heating or cooling apparatus or unit may use a heat sink in conjunction with a fan to dissipate heat produced during temperature changes. The heating or cooling apparatus or unit may use a radiator and liquid cooling/circulating system to dissipate heat produced during temperature changes. The heating or cooling apparatus or unit may use temperature sensors or thermistors as a means of providing temperature feedback to a control system, which may be a microcontroller or other electronic circuit. The bulk reagent reservoirs may be connectorized, such as by split septum, enabling facile exchange of individual reservoirs. Other connector types include, but are not limited to, Luer locks, ¼ 28, MINSTACK (LEE Co).

The device may include a mechanism of extracting liquid from a flow cell. According to one aspect, a vacuum is generated by a pump, such as a main pump or syringe pump, which is used to aspirate liquid contained in a flow cell, such as an open well or partially enclosed flow cell.

According to one aspect, a motorized sipper tube is used to contact the sample holder or liquid therein for the purpose of extracting liquid. Further according to this aspect, the motorized sipper tube may comprise a pneumatic, servo, or stepper motor, a positional encoder, and electromechanical controller system. The device may contain one or more waste liquid repositories, into which waste or extracted liquid is directed for the purpose of temporary storage. Waste liquid may be directed by means of pumps and valves, such as a rotary valve. The waste liquid repository may comprise a feedback system for automatically notifying a user upon reaching a certain level. The waste liquid may be directed to one or more repositories based on the nature of the reagent, to prevent undesired chemical reactions, or to facilitate downstream disposal according to applicable procedures, laws, or regulations.

The device may include a mechanism of covering one or more flow cells, wells, sample holders and/or stages for the purpose of preventing accumulation of airborne particulates in the sample and/or preventing evaporation of liquid reagents. According to one aspect, the device contains a motorized flowcell cover that uses one or more motion axes to position an airtight cover over one or more flow cells, wells, sample holders and/or stages. According to another aspect, the stage contains a dynamically extendable cover. According to another aspect, the device contains a static cover capable of interfacing with the motorized stage for the purpose of enclosing the wells and/or sample holders.

The device may include an optical assembly including one or more optical axes. The device may include one or more detectors, such as large area detectors, for volumetric imaging of the three dimensional nucleic acid containing matrix. The detectors may be cameras, and in particular, cameras with physical attributes tailored to high-speed, low-noise scientific imaging, such as an sCMOS camera. In one such embodiment, a reflection based autofocus system provides closed loop control of the optical axis in order to attain and/or maintain sample focus. In another configuration, a microcontroller, FPGA, or other computing device may provide software focus and positioning feedback using one or more image analysis algorithms such as that described in Mario, A. Bueno, Josue Alvarez-Borrego, and L. Acho. "Autofocus algorithm using one-dimensional Fourier transform and Pearson correlation." 5*th Iberoamerican Meeting on Optics and* 8*th Latin American Meeting on Optics, Lasers, and Their Applications*. International Society for Optics and Photonics, 2004 hereby incorporated by reference in its entirety. Such automated sample positioning may include coordination of one or more motion axes in conjunction with the imaging system. The sample positioning may account for physical shifts in sample position over the course of imaging and may be tolerant of shifts that are greater than the field of view captured in a single image frame. The device may implement a means of mapping a planar surface, rendering the need for autofocusing in real time unnecessary. Such a system may include using a reflection- or software-based autofocus system to sample three or more points at the sample surface and then fitting those points to the equation for a plane or the surface geometry of the solid substrate. The fitting process may involve excluding one or more points based on autofocus signal data, its residual as a result of regression analysis, or other factors indicating its fitness as a data point. The fitting process may include allowances for surface variance consistent with the sample mounting medium, such that the final surface map may include local deviations from a perfectly flat plane to reflect variations in the actual substrate surface. As described in FIG. 12, according to one aspect the device comprises a system for mapping the surface of a sample holder with respect to one or more motion axes for the purpose of reproducible positioning of the sample relative to the imaging system, comprising the steps of using: 1) an autofocus system, such as a laser-reflection autofocus mechanism, to acquire one or more distance measurements between the optical system and the sample, and 2) computing one or more offsets relative to the positional encoder(s) along the one or more motion axes, which are used during image acquisition.

The device may use image-based software programs for determining, adjusting, correcting, and/or tracking the position of the sample. According to one aspect, image data is computationally registered to a reference for the purpose of calculating a positional shift along one or more dimensions. Further according to this aspect, a Fourier transform (FT), such as the discrete Fourier transform (DFT) or fast Fourier transform (FFT) is used to compute a shift between two or more images or image volumes along one or more dimensions. According to one aspect, sub-pixel shifts are calculated, such as by using the upscaled DFT. According to one aspect, translational shifts are calculated along one or more dimensions. According to another aspect, rotational shifts are calculated along one or more dimensions. According to one aspect, features or fiducial markers contained within the sample holder, flowcell, well, or sample, are used for the purpose of aiding positional tracking using image analysis. Features or fiducial markers include features manufactured into or added onto the sample holder, flowcell, or well, such as engraved features, laser-engraved features, printed features, deposited features, microcontact printed features, beads, and other types of patterns in one or more dimensions. According to one aspect, fiducial markers are embedded into the sample, such as into the 3D hydrogel. According to one aspect, the fiducial markers are microscopy beads, which may be fluorescent or autofluorescent. According to one aspect, features are an aspect of one surface of the solid substrate forming part of the sample holder. According to a certain aspect, the features are an aspect of a different surface of the sample holder than the surface containing the sample. In one example, the flowcell is understood to be a glass slide containing two or more open wells on the top surface, with beads serving as fiducial markers deposited on either the top or bottom surface of the glass slide.

A microcontroller system coordinates motion systems in XYZ axes along with the illumination/excitation light source and camera sensor such that the motion systems position the sample relative to the optical system, then image data is acquired at that position with global shutter capture or rolling shutter or "all lines firing" rolling shutter capture using synchronized illumination. In other cases, the motion along one or more axes are synchronized with the capture of lines along the camera sensor such that the sample does not need to come to a resting position relative to the optical system. Software and hardware handshaking protocols are implemented over low-latency communication protocols (e.g., digital TTL, I2C, RS-232, UDP, TCP/IP) to coordinate between the subsystems, e.g. initiating axis motion or triggering a camera exposure.

The device may include one or more objective lenses for imaging. In a certain aspect, the device may include one objective lens. In another aspect, the device may contain two objective lenses. In another aspect, the device may contain three or more objective lenses. The objective lenses may be water immersion lenses, oil immersion lenses, water dipping lenses, air lenses, lenses with a refractive index matching another imaging medium, or lenses with an adjustable refractive index. In a certain aspect the device contains a single water dipping objective lens, which provides for higher image quality by eliminating the refractive index mismatch occurring at the interface between two media with distinct refractive indexes, such as an air-water interface or water-glass interface.

In aspects comprising one or more objective lenses with refractive index not matched to air, the objective lens must interface with an imaging media, such as water, oil, or other imaging buffer. In these aspects, the device may comprise a mechanism of wetting the objective lenses or otherwise creating an interface between the objective lens and the imaging medium. Certain mechanisms of lens wetting include dipping the lens into an imaging medium or otherwise dispensing an imaging medium onto the lens, such as by a syringe, needle valve, or other mechanisms known to those familiar with the art of dispensing a liquid reagent. In a certain aspect, the device dispenses a certain amount of liquid into a well for the purpose of creating an incident angle between the objective lens and the liquid interface for deposition of liquid onto the objective lens without forming bubbles. In another aspect, the device dispenses a certain amount of liquid onto the objective, such as by using a syringe or needle valve, without forming bubbles, as by controlling the speed and angle of incidence between the liquid droplet and the objective lens.

During imaging in a liquid imaging medium, bubbles may form either on the objective lens, within the sample, or between the objective lens and the sample; including in devices imaging within an open flowcell and through a glass interface present in a closed flowcell. The device may contain a mechanism of detecting bubbles formed on the objective lens, or bubbles present between the objective lens and the sample. Mechanisms of bubble detection include detection via scattering of light; by image analysis, e.g., by measurement of the point spread function of the optical system, which is perturbed by bubbles; by external machine vision, such as by a camera or other imaging system observing the lens, connected to a computer system with software programmed to detect bubbles on the lens. The device further may contain a mechanism for eliminating bubbles formed on the objective lens. According to one aspect, the device comprises a mechanism for contacting the objective lens with an aspirating needle, which removes any liquid present on the objective lens. According to another aspect, the device comprises a mechanism for contacting the objective lens with an absorbent material, which absorbs any liquid present on the objective lens. The device may contain a mechanism for drying or removing liquid from the objective lens. The device may execute a software and hardware routine for removing and replacing a liquid imaging medium from the lens upon detection of a bubble. The device may contain a mechanism for alerting a user upon detection of bubbles on the objective lens, within the sample, or between the objective lens and the sample.

During operation of the device, the objective lens may accumulate dirt, dust, deposited salts or other reagent solutes, or other types of materials which interfere with imaging. The device may contain a mechanism for detecting such interference, via scattering of light or other properties of the interaction between light and the interfering material; by image analysis, e.g., by measurement of the point spread function of the optical system, which is perturbed by the presence of interfering materials; by external machine vision, such as by a camera or other imaging system observing the lens, connected to a computer system with software programmed to detect interfering materials on the lens. The device may further contain a mechanism for cleaning the objective lens. According to one aspect, the device may include a lens cleaning reagent, which is dispensed onto the lens for the purpose of cleaning the lens, such as by a syringe or needle valve, or by dipping the objective lens into a cleaning reagent dispensed into a well or onto a non-abrasive material, which is made to contact the objective lens. The device may contain a mechanism for alerting a user upon detection of an interfering material on the objective lens, within the sample, or between the objective lens and the sample.

The device comprises one or more optical light paths. The device may contain optics for the purpose of correcting refractive index mismatches between certain components of the optical system and the sample or imaging medium. The device may contain optics for the purpose of correcting other types of optical distortion within the optical system, such as spherical or chromatic aberration. The device may contain a mechanism of detecting optical distortion, such as by using an image sensor combined with software to detect changes in a point-spread function of the optical system or other property of the optical system. According to one aspect, the device comprises one or more beam characterizing cameras. According to another aspect, prior to, during, or after operation of the device, the device may contain an automated or manual routine for measuring the point spread function or other optical property of the system and alerting a user or engaging a mechanical, electromechanical, or optical system for correcting the optical distortion. According to a certain aspect, the device contains an adaptive optical system (AO), which is used to improve the performance of optical systems by reducing the effect of wavefront distortions. Adaptive optics can correct deformations of an incoming wavefront by deforming a mirror in order to compensate for the distortion. The adaptive optics system may comprise a deformable mirror, image sensor, and hardware and software feedback systems. According to one aspect, the adaptive optic system contains a wavefront sensor, such as the Shack-Hartmann wavefront sensor. The adaptive optical system and other corrective optical systems may be open loop, where errors are measured before they have been corrected by the corrector. The adaptive optical system and other corrective optical systems may be closed loop, where the errors are measured after they have been corrected by the corrector. Adaptive optics may be used to improve the image quality within a 3D sample by correcting for optical aberrations within the sample.

The device may include one or more electromechanical, electronic, or fully computerized systems for the purposes of controlling and coordinating the timing of fluidic, optical, and motion-related events. Device subsystems such as motor controllers, temperature controllers, pneumatics controller, valve controllers, cameras, optical tuning or gating systems, sensors, and other electronic systems may leverage a variety of communication protocols for the purposes of such coordination. Communication protocols may be selected on the basis of latency, interoperability, electromechanical constraints or other application-focused considerations. Subsystems may conform to consistent or well-defined application program interfaces (APIs) such that they may be individually addressed and/or operated from generic computers or human machine interfaces.

Timing of optical systems such as cameras, confocal optical systems, illumination devices, AOTFs, mechanical shutters, etc, and single- or multi-axis motion control systems may be coordinated by microcontrollers, motor controllers, electronic circuits, and/or computerized systems. Optical sensor exposure timing may be optimized such that motion control movements overlap with non-measurement sensor events such as pixel readin/readout or background measurements. Optical illumination timing (e.g., laser illumination gated) may be implemented such that it is tied to specific optical sensor events (e.g., readin/readout) so as to minimize sample exposure to excitation light. Single- or multi-axis motion control for the purposes of optical imaging may be further optimized to account for the sensor exposure regimen (e.g., rolling shutter exposure) for continuous motion applications. Under certain specialized imaging regimes, e.g., time delay integration (TDI), it is possible to execute continuing axis motion during the acquisition of imaging data.

In certain aspects, the dimension order of multi-axis motion control (when coupled with optical imaging) may be selected so as to minimize frame-to-frame move times. For example, it is often the case the vertical axis (i.e., Z or optical axis) move times are the fastest, so it is desirable to perform three-dimensional imaging in a series of "Z stacks" in which frames are acquired while the vertical axis is driven up or down. These Z stacks are performed repeatedly across an X/Y plane or plane-like surface in order to acquire a fully three-dimensional volume of image data.

In some cases, it may be desirable to image a three-dimensional volume that is not cuboid in nature. In these cases, a three-dimensional coordinate system based on physical or engineering units may be employed to dictate arbitrary three-dimensional imaging positions that are then disseminated to the participating motion control and imaging systems. Employing such a system allows for imaging that is constrained exclusively to the region of a three-dimensional matrix in which sample voxels of interest exist.

It may be desirable to image the volume with a particular spatial sampling frequency. In certain aspects, the sampling frequency of imaging along one or more axes is determined relative to the Nyquist frequency of the optical system. In a certain implementation, image data acquired using a 40×1.0 NA objective is sampled in the axial (Z) axis at approximately 500 nanometer intervals. In another aspect, the sampling frequency of imaging along one or more axes is oversampled, such as by acquiring image data or sampling the same area of the sample volume twice. Further according to this aspect, oversampling the volume may facilitate computational volumetric reconstruction, such as by providing redundant image data in neighboring image frames for the purpose of volumetric image stitching. In a certain implementation, image data may be acquired with 10% overlaps along one or more axes, with 20% overlaps along one or more axes, or with 30% or more overlapping pixel data along one or more axes.

The device may include more than one stage, fluidics unit, and/or optical system such that each sample holder and/or sample may be addressed by multiple systems. Under such a regime access to certain hardware resources must be shared and therefore a physical resource allocation and scheduling system is necessary. Such a scheduling system may be passive or active, and may include predictive modeling as a means of anticipating and scheduling hardware resource access based on future fluidic and optical imaging needs on a per-sample basis. Further aspects of the scheduling system may allow for external events, such as those performed by a user or an external computer system to interrupt or otherwise modify the activities of the fluidic imaging system. In one such aspect, a physical media storage system may become full and no longer able to store acquired images. This event could trigger a cessation of imaging activities on the device pending external user intervention. In another aspect, a user may want to add a sample in a sample holder to a slot on a device stage. The user may be able to, through an HMI, graphical user interface, or using a physical button, temporarily pause or otherwise modify the operational state of the device to allow for the addition of the sample holder.

The device may be operated and otherwise programmed through a command line interface, graphical user interface, or application programming interface (API) exposed through local software libraries over a network connection. The user may be able to perform activities including but not limited to: physical configuration of the device, testing and calibration tasks, sample holder and sample definition generation and modification, fluidic manipulations and routine specification, optical measurement and routine specification, sequencing protocol development, as well as other tasks related to general fluidics, optical imaging, and motion control. The device may include hardware or software that enables real time analysis of imaging data, such as FPGAs or user-space software running on GPUs that allows for activities such as three-dimensional image alignment, objective finding, signal processing or measurement, and other image analysis tasks as required by sequencing and optical sample analysis. The device may include hardware and software designed to store image data locally. The device may be part of a network of devices and services designed to collect, analyze, store, and visualize three-dimensional imaging and sequencing data. This network may include physically co-located hardware as well as cloud computing faculties. In certain embodiments it may implement open standards to interface with third party hardware and software.

It is to be understood that the device includes software to automate the procedures of amplification and sequencing as described herein. It is to be further understood that the hardware components described herein are commercially available in whole or in part. According to one aspect, a commercially available sequencing apparatus called the "115 Pollinator" manufactured by Danaher Corporation may be used for the sequencing aspects described herein and may be modified to include the hardware for volumetric imaging described herein.

This invention is further illustrated by the following examples, which should not be construed as limiting. The contents of all references, patents and published patent applications cited throughout this application are hereby incorporated by reference in their entirety for all purposes.

Example I

Figure 2:
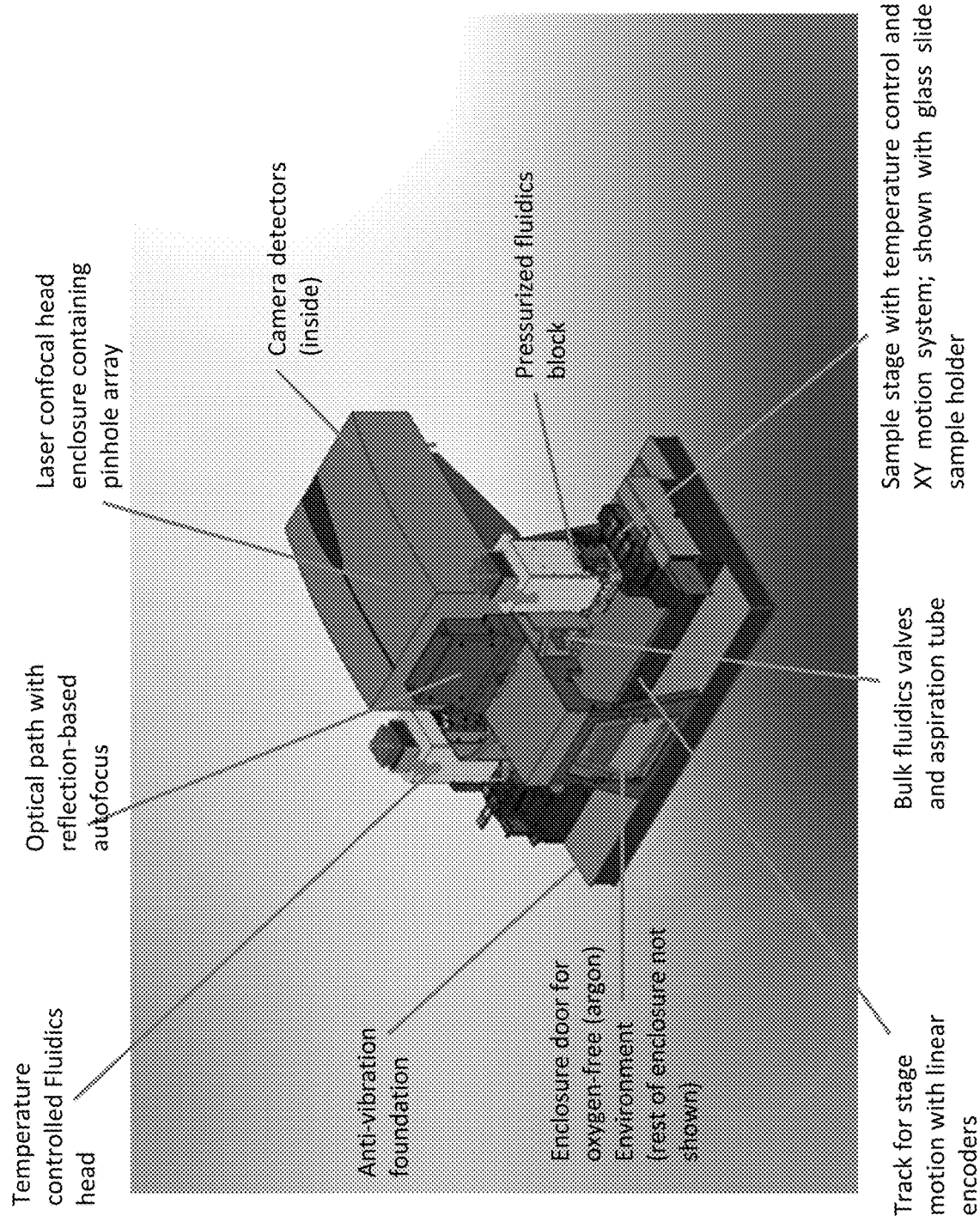
FIG. 2 is a perspective view in schematic of components of an automated sequencing and three-dimensional volumetric imaging device.

Operative Components of an Automated Sequencing and Three-Dimensional Imaging Device FIG. 2 is a perspective view in schematic of operative components of an automated sequencing and three-dimensional imaging device of the present disclosure. It is to be understood that further components may be added to the device including housing elements. As shown in FIG. 2, the automated sequencing and three-dimensional imaging device includes a laser confocal head enclosure including a pinhole array and camera detectors for receiving light from the sample. Such a hardware arrangement allows for volumetric imaging of a three dimensional nucleic acid containing matrix. The device further includes an optical path with reflection-based autofocus to the laser confocal head enclosure. The device further includes a temperature controlled fluidics head on a pressurized fluidics block which serves to provide one or more reagents to the sample. Operatively connected bulk fluidics valves and an aspiration tube for removing liquid from the sample are provided. A sample stage with temperature control and XY motion system is provided and is shown with a glass slide sample holder. A track for stage motion with linear encoders is operatively connected to the stage. An enclosure door for an oxygen-free (argon) environment is provided with the rest of enclosure not shown. The device rests on an anti-vibration foundation.

Figure 3:
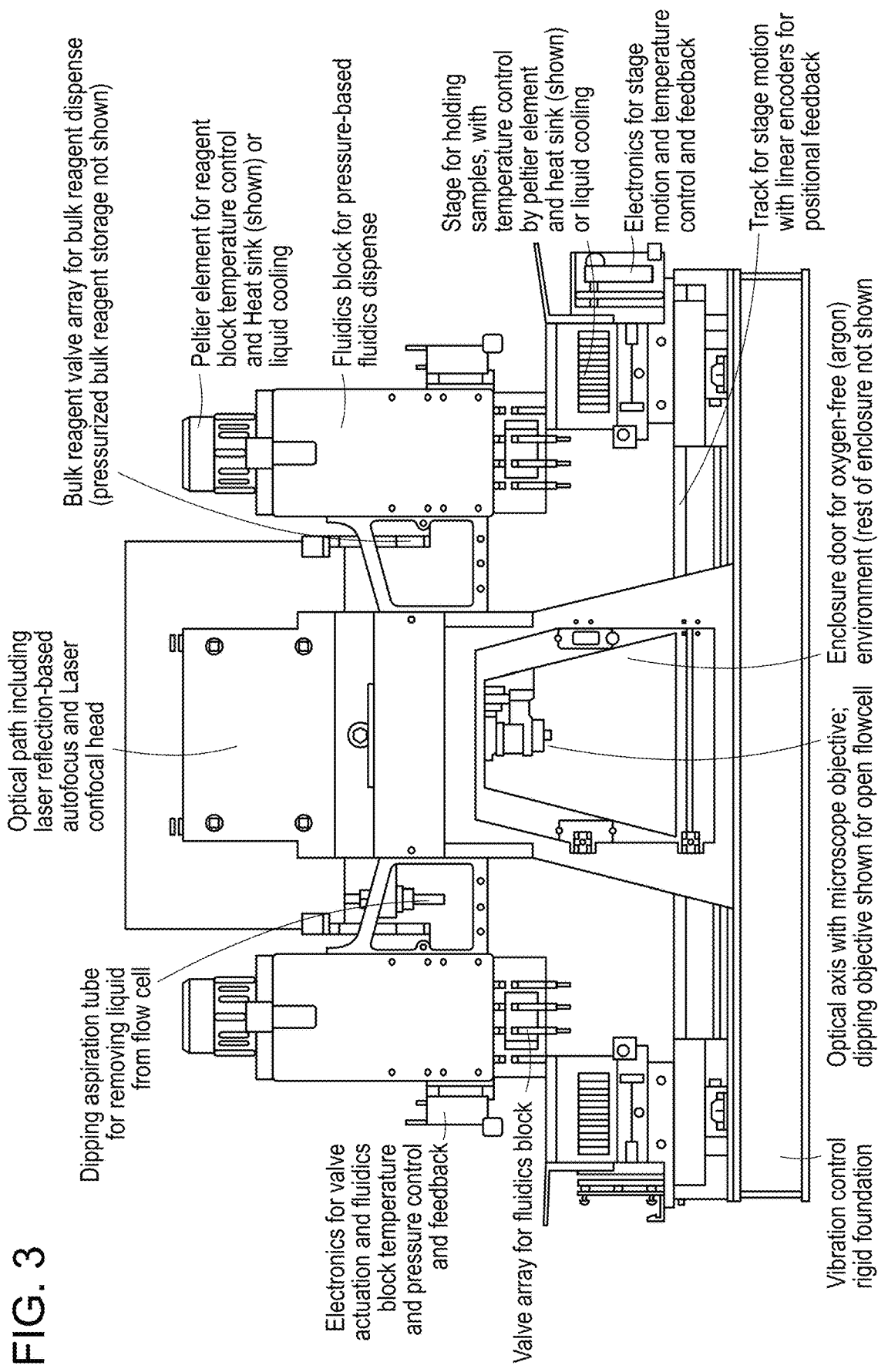
FIG. 3 is a front view in schematic of components of an automated sequencing and three-dimensional volumetric imaging device.

FIG. 3 is a front view in schematic of operative components of an automated sequencing and three-dimensional imaging device of the present disclosure. The device includes an optical path including laser reflection-based autofocus and a laser confocal head. A bulk reagent valve array for bulk reagent dispense is shown (pressurized bulk reagent storage not shown). A Peltier element for reagent block temperature control and heat sink (shown) or liquid cooling is shown connected to a fluidics block for pressure-based fluidics dispense. A dipping aspiration tube for removing liquid from the flow cell is shown. Electronics are provided for valve actuation and fluidics block temperature and pressure control and feedback. A valve array is shown connected to the fluidics block. A stage for holding samples, with temperature control by Peltier element and heat sink (shown) or liquid cooling is provided. Electronics for stage motion and temperature control and feedback are provided. Track for stage motion with linear encoders for positional feedback is provided. An optical axis with microscope objective is shown. A dipping objective is shown for open flowcell. An enclosure door for oxygen-free (argon) environment is provided (rest of enclosure not shown). The device includes a vibration control rigid foundation. As can be seen in FIG. 3, the device for volumetric imaging of a 3D sequencing matrix utilizes two independent stages and two independent fluidics systems along with a single optical axis for image acquisition. Image acquisition is in practice the temporally limiting step. No matter how long the biochemistry and fluidics for sequencing take per base, this is a fixed time per base (e.g. 2 hours), but the imaging time is proportional to the size of the volume being imaged. By using two stages, each operating independently and with independent fluidics, one stage can be doing biochemistry/fluidics while the other stage is imaging. Therefore the system is always effectively waiting to image and the fixed biochemistry time is effectively zero as the system is never waiting on fluidics to complete in order to proceed to the next step, but is always waiting on imaging to complete. Scan time may be an issue for 3D optical scanning vs. 2D optical scanning, as 2D scan time increases to the second power with scanning area, but in 3D scan time increases to the third power with scanning volume. The configuration of two independent stages and two independent fluidics systems along with a single optical axis for image acquisition is also cost effective, as the stage with motion/temperature control stage and fluidics subsystems are relatively cheap compared to the optical subsystem, which requires costly optics, camera detectors, data acquisition electronics (e.g. frame grabber hardware to capture image data from the cameras), and laser sources for fluorescent excitation.

Figure 4:
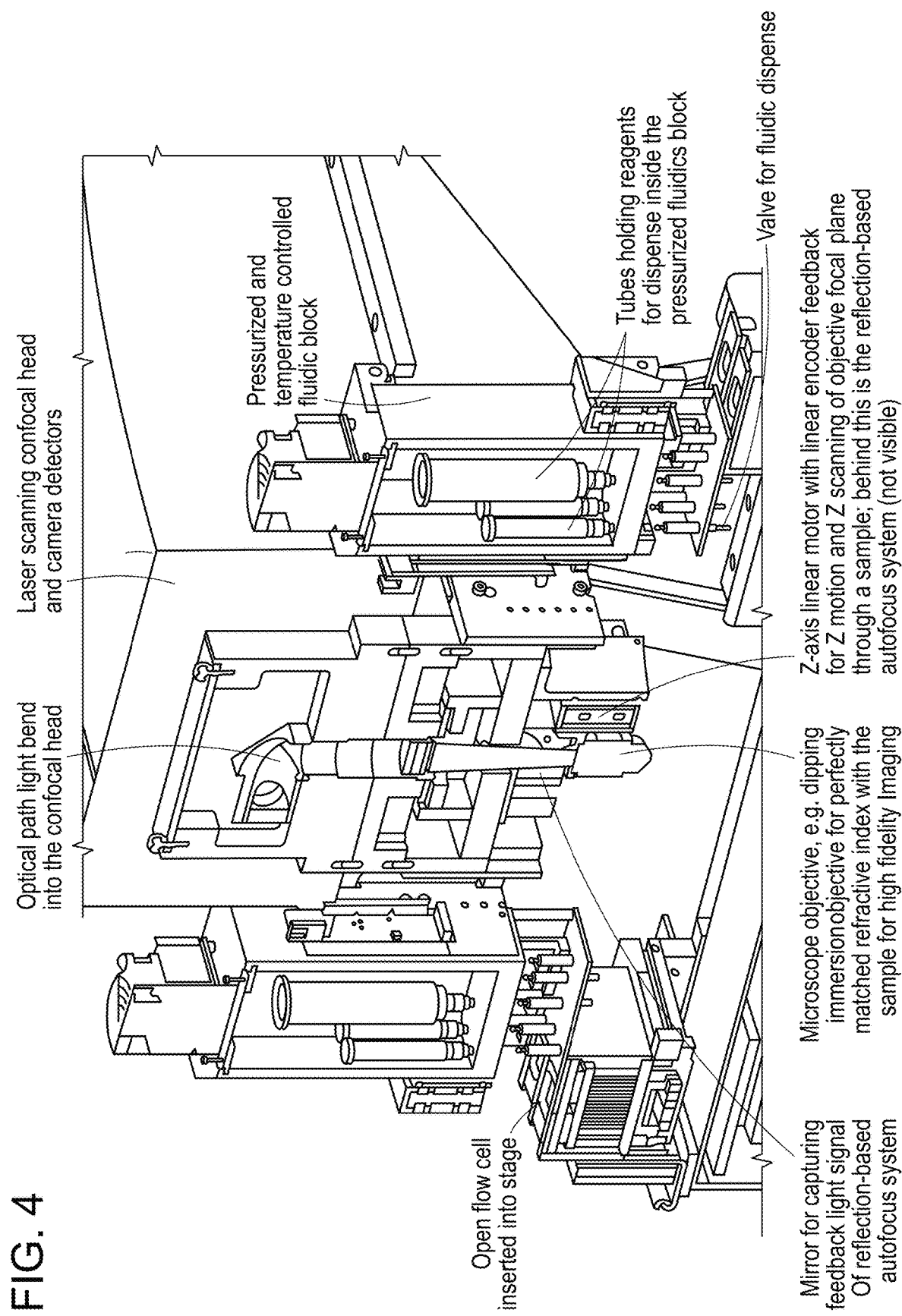
FIG. 4 is a perspective view in schematic of components of an automated sequencing and three-dimensional volumetric imaging device.

FIG. 4 is a perspective view of the device of the present disclosure. Laser scanning confocal head and camera detectors are provided. An optical path light bend into the confocal head is provided. A microscope objective is shown, e.g. a dipping immersion objective for perfectly matched refractive index with the sample for high fidelity imaging. A mirror for capturing feedback light signal of reflection-based autofocus system is provided. An open flow cell is shown inserted into the stage. A Z-axis linear motor with linear encoder feedback for Z motion and Z scanning of objective focal plane through a sample is provided. Located behind the Z-axis linear motor is the reflection-based autofocus system (not visible). A pressurized and temperature controlled fluidic block is shown. A valve for fluidic dispense is provided. Tubes holding reagents for dispense are shown inside the pressurized fluidics block.

Figure 5:
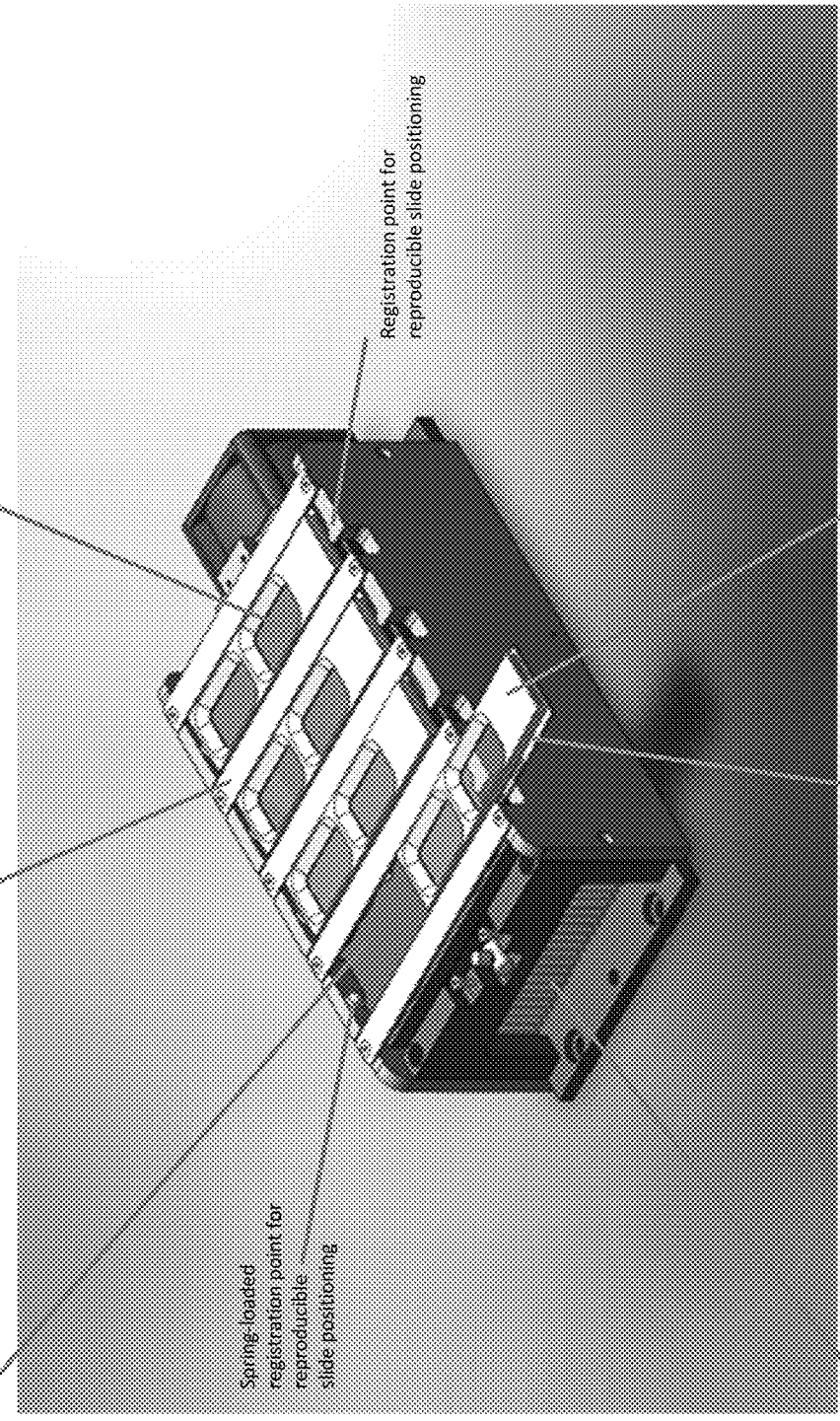
FIG. 5 is a perspective view in schematic of a stage with sample holders of an automated sequencing and three-dimensional volumetric imaging device.

FIG. 5 is a perspective view of a stage according to the present disclosure. A heat sink for the Peltier cooler for stage temperature control is provided. A flow cell foundation is shown as a standard 1×3 inch 1 mm thick glass microscopy slide onto which the 3D sequencing library matrix is attached. The 3D sequencing library matrix attached inside the well. A fluidic well component of the open-format flowcell is shown as a 2-well format. An open-format flowcell avoids problems with bubbles and laminar flow over irregular 3D matrix that would cause uneven diffusion of reagents into and out of the 3D sequencing library matrix. A spring-loaded registration point for reproducible slide positioning is provided. The flow cell contacts a thermocycling stage top. A rail system for reproducible slide positioning is provided that provides 2D directional force onto the slide (downward and along one of the long edges of the slide) and secures the sample. A registration point for reproducible slide positioning is provided. In one implementation, the flow cell consists of a series of open-chambers or wells. Reagents are dispensed into the wells from the top by the fluidic system and removed by an aspiration tube. Open well format is preferable for 3D matrix samples as formats enclosed on top and bottom may suffer from issues related to fluid dynamics such as uneven laminar flow over an irregularly-shaped 3D matrix, and introduction or trapping of bubbles by vortexes created in the dynamic liquid field. Open well format is amenable to upright (from the top) microscopy modalities by one or more optical axes where the objective physically dips into an imaging medium such as an imaging buffer, minimizing or eliminating refractive index mismatches between the optical system and the sample (e.g. air/glass interface).

Figure 6:
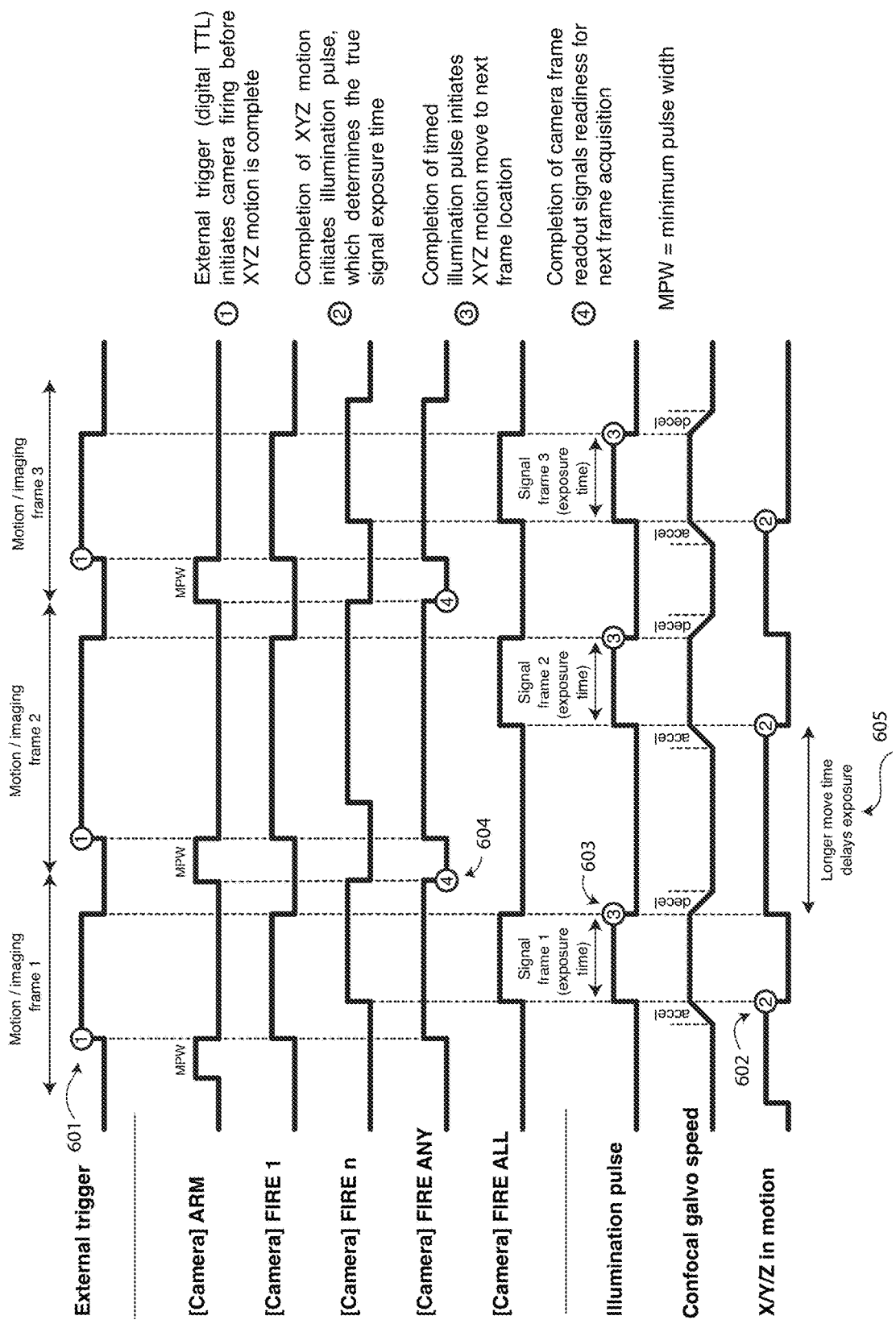
FIG. 6 is an exemplary schematic timing diagram useful with embodiments described herein.

FIG. 6 is a schematic timing diagram illustrating an example of coordination between optical imaging, illumination, motion control, and acquisition systems for the purposes of achieving optimal imaging frame rates.

Figure 7:
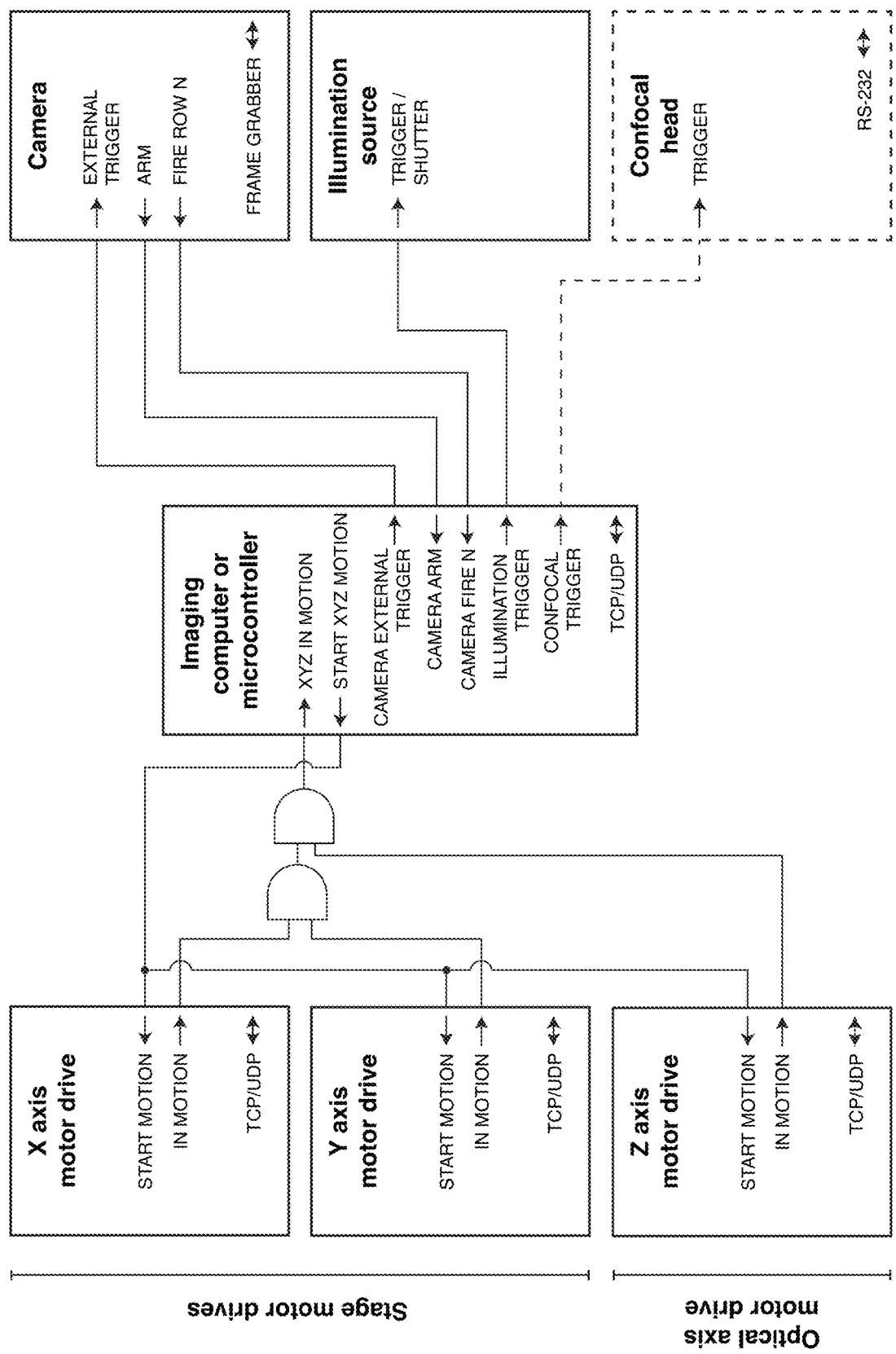
FIG. 7 is an exemplary schematic block diagram illustrating aspects of an exemplary TTL communication structure.

FIG. 7 is a schematic block diagram illustrating an example TTL communication structure for the purposes of optimal real time coordination of optical imaging, illumination, motion control, and acquisition systems.

Figure 8:
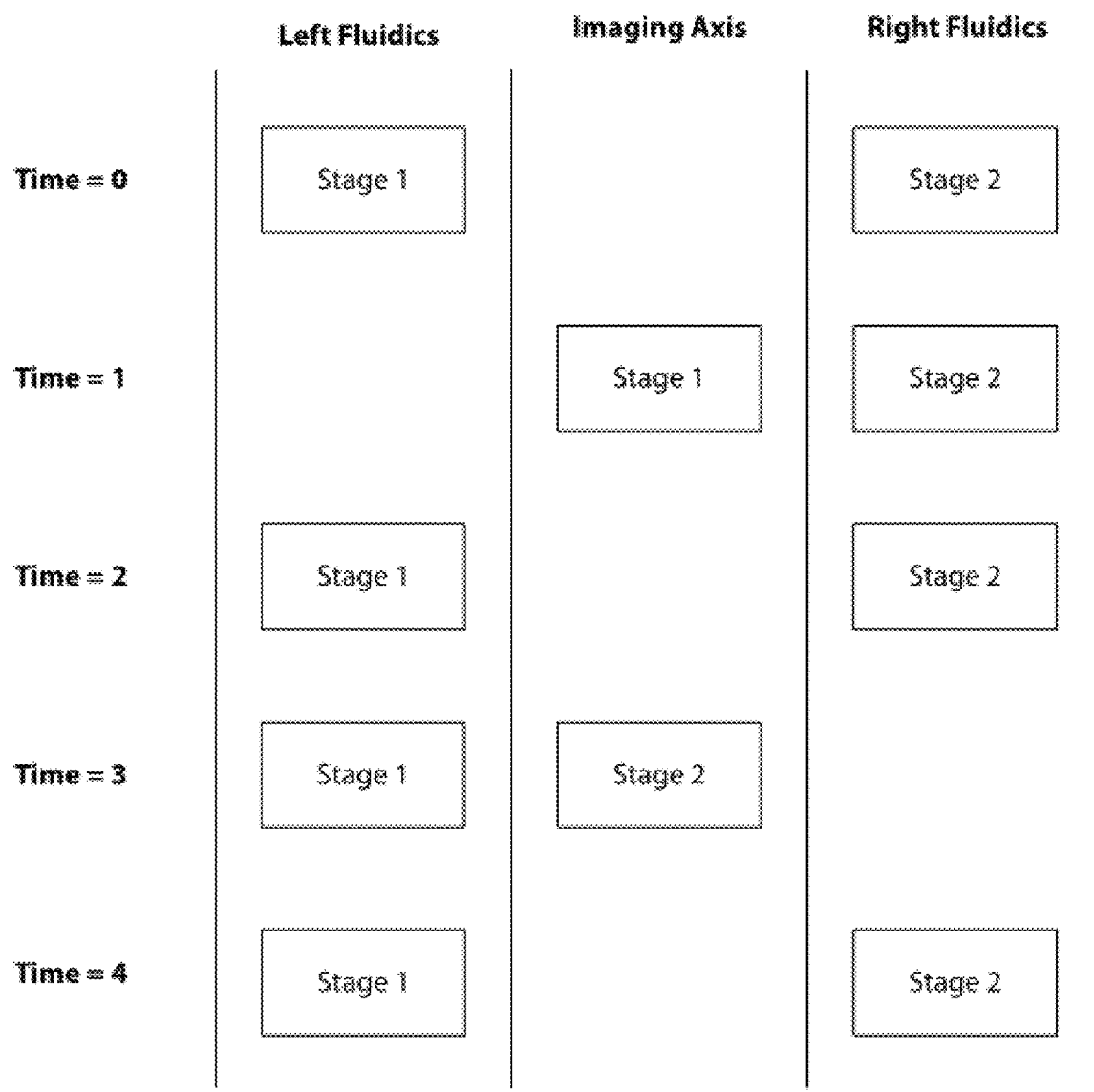
FIG. 8 depicts an exemplary timing and resource usage timing diagram for sequencing device fluidics, imaging, and dual stage subsystems.

FIG. 8 depicts the timing and resource usage timing diagram for sequencing device fluidics, imaging, and dual stage subsystems. This figure depicts a device with two independent motion stages, which house the sample holders, two intendent fluidic systems, denoted "Left" and "Right", and a single imaging axis. A controller manages the motion stages such that at Time=0, both stages are engaged in fluidic routines. At Time=1, image data is acquired from the samples on Stage 1 while Stage 2 is engaged in fluidic routines. At Time=2, image data acquisition from Stage 1 has completed, and fluidic routines for Stage 2 have completed. At Time=3, image data is acquired from the samples on Stage 2, while Stage 1 is engaged in fluidic routines. At Time=4, image data acquisition from Stage 2 has completed, and fluidic routines for Stage 1 have completed.

Figure 9:
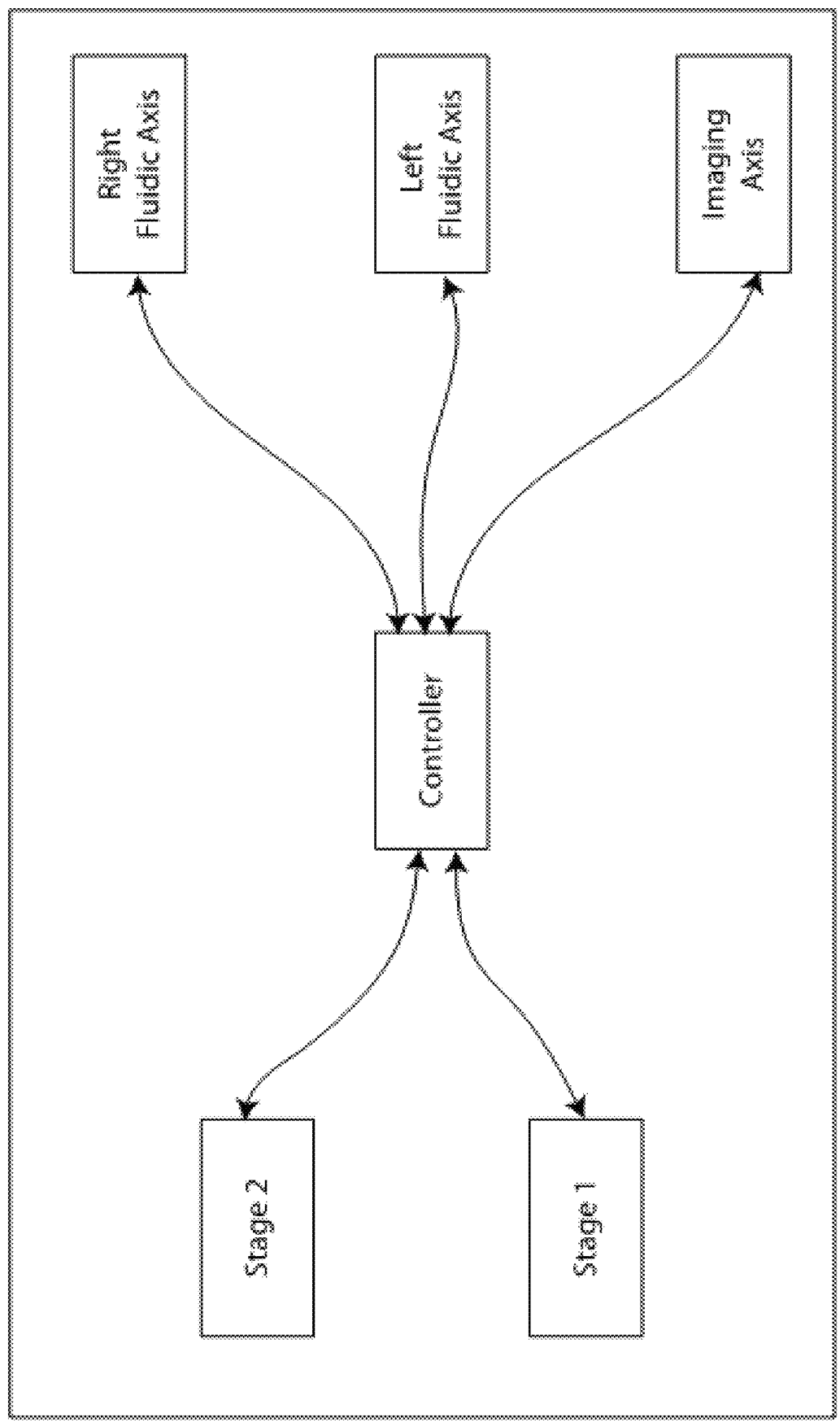
FIG. 9 depicts an exemplary schematic block diagram illustrating the controller organization for the dual stages, fluidic, and imaging subsystems.

FIG. 9 depicts a schematic block diagram illustrating the controller organization for the dual stages, fluidic, and imaging subsystems. A controller synchronizes event timing, such as that depicted in FIG. 8.

Figure 10:
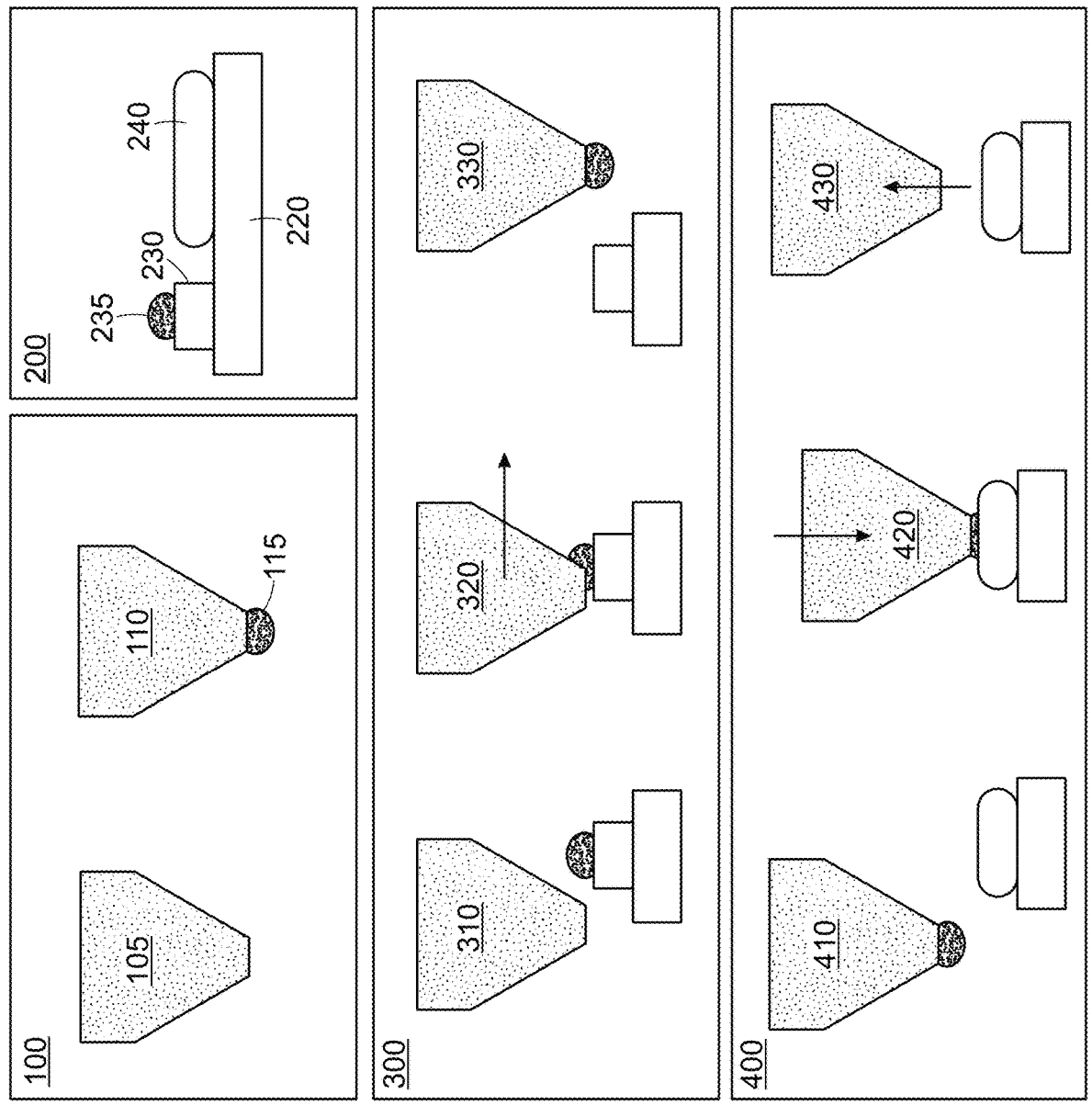
FIG. 10 depicts exemplary device systems for managing the state of and interfacing with an objective lens.

FIG. 10 depicts device systems for managing the state of and interfacing with an objective lens. Subpanel 100 is directed to depiction of a dry objective (105) and a wet objective (110) comprising the objective lens with a droplet of imaging medium (115). Imaging medium include aqueous imaging buffers, such as water and anti-fade reagents, as well as oil and other types of imaging liquids. Subpanel 200 depicts a configuration of an apparatus for objective wetting and drying, such as an apparatus for removing a bubble from an objective lens or for cleaning an objective lens; a carrier is depicted (220), which may be a fixture of the device or a consumable insert, which further comprises a modality (230) for depositing a reagent (235) onto the objective lens, such as a well or reagent dispensing apparatus, and also further comprises a modality (240) for removing liquid from an objective lens, such as a non-abrasive absorbent material or aspirating port. Subpanel 300 depicts a routine for depositing liquid onto an objective lens, comprising the steps of forming a liquid interface on the liquid wetting modality (310), contacting the objective lens with the liquid interface (320), as by translating the objective lens or objective wetting modality, such that the objective is wetted (330). Subpanel 400 depicts a routine for removing liquid from an objective lens (410), comprising the steps of translating the objective lens or drying modality such that the drying modality contacts the liquid forming an interface (420) such that the liquid is absorbed or otherwise aspirated by the drying modality, resulting in an objective lens without a liquid droplet (430).

Figure 11:
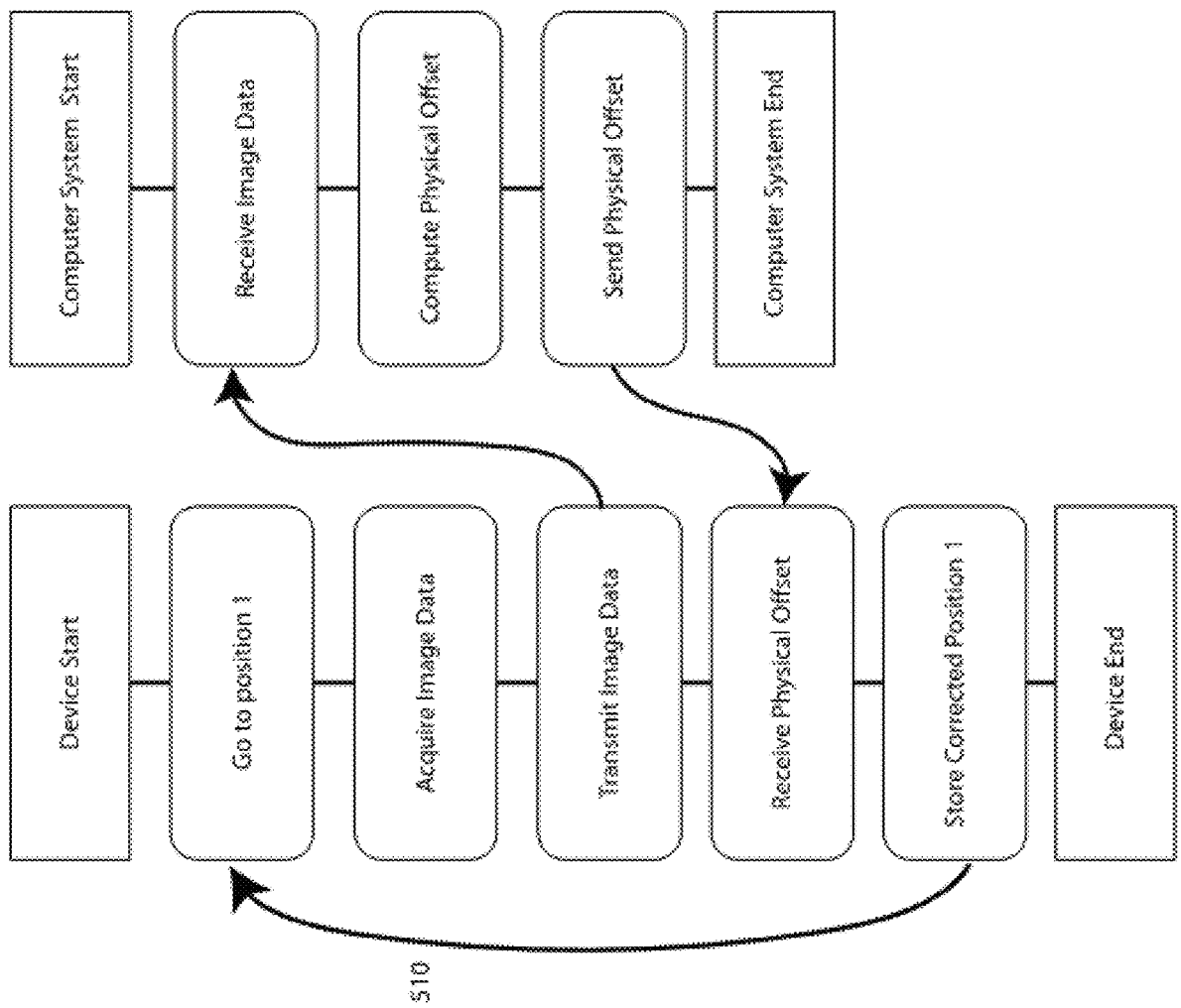
FIG. 11 depicts a flow chart for repeatable XYZ positioning of the sample relative to the imaging axis over time.

FIG. 11 depicts a flow chart for repeatable XYZ positioning of the sample relative to the imaging axis over time. In the case where the solid substrate may shift over time, this system for determining shifts of a sample holder can increase the accuracy of XYZ positional repeatability over time between the sample and the imaging system. At the initialization of imaging, the device moves Position 1 under the imaging axis and acquires initial image data, which is transmitted to a computer system. The Computer system computes a physical offset relative to a reference image dataset, which is communicated to the Sequencing Device and stored. As depicted in Loop 510, the sequencing device may repeat these steps until the physical offset received by the computer system is lower than a threshold amount, e.g., until the computer system confirms the physical positional information stored by the device corresponding to Position 1 is within a given physical shift relative to a reference positional state.

Figure 12:
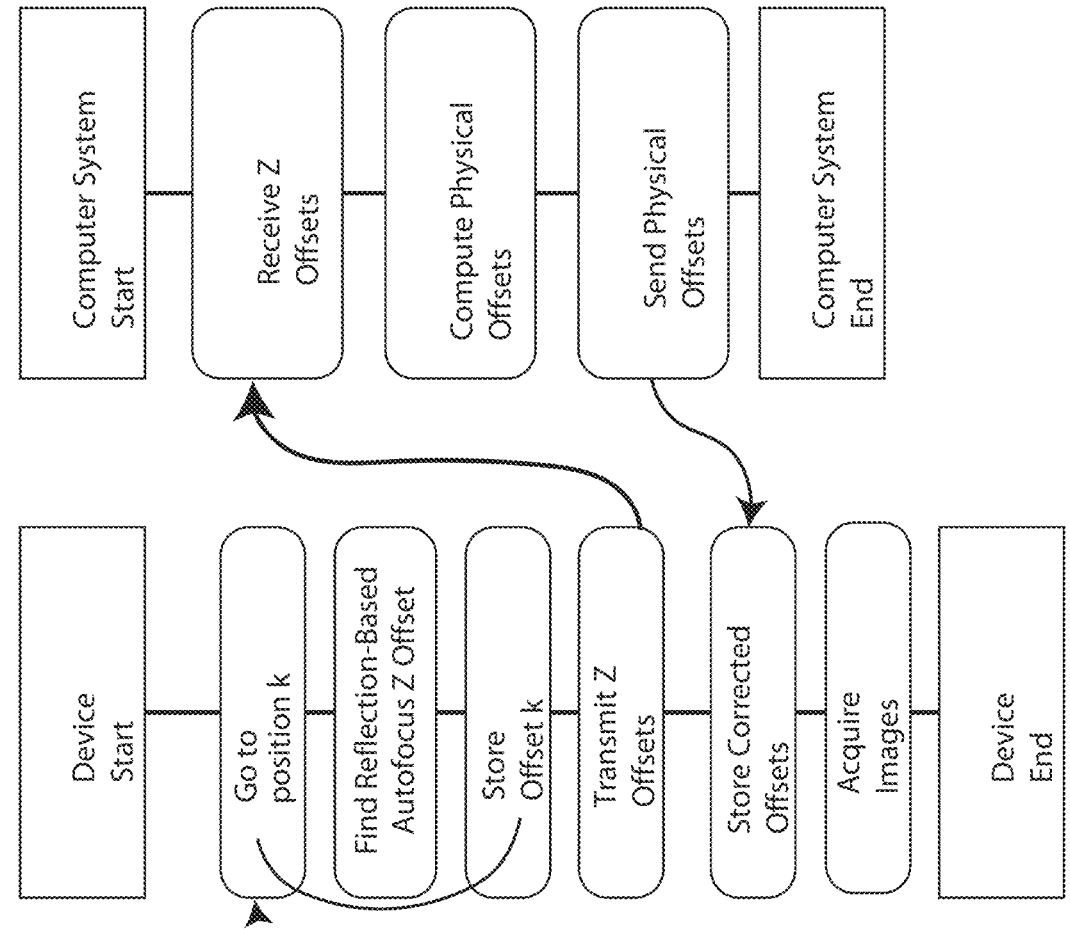
FIG. 12 depicts an exemplary system for mapping a surface of a sample holder comprising a solid substrate.

FIG. 12 depicts a system for mapping a surface of a sample holder comprising a solid substrate. In the case where the solid substrate may shift over time and a particular autofocus system may have a certain failure rate, this system for mapping the surface of a sample holder can increase the accuracy of Z positional repeatability over time between the sample and the imaging system, such as by discarding outliers in the Z offsets as determined by the autofocus system. This system may also increase image acquisition speed, as pre-computing physical offsets for the motion system may be significantly faster than allowing the autofocus to determine the physical offset in real time at each potential imaging position. Panel 600, which includes Subpanels 610, 650, and 700, depicts a diagram of the device state. In Subpanel 610, an objective lens (620) is positioned relative to a solid substrate (630), such as glass, silicon, metal, plastic, or another solid material, which is understood to immobilize a mounted sample such as a FISSEQ hydrogel. This depiction includes a laser-based autofocus device, which shines a laser (640) onto the solid substrate in order to determine the distance between the objective and the solid substrate, such as by analyzing the reflection of the laser light from the surface. Subpanel 650 depicts a side view of subpanel 610, wherein the distance 680 between the objective and the solid substrate corresponds to a known value, such as the focal length of the objective, when the objective lens is determined to be focused on the solid surface. Subpanel 700 depicts scanning the objective (710) in one, two, or three axes (715 depicts three possible motion axes) over the solid substrate (720), such that an Z autofocus offset is measured at each scan position (730). Subpanel 900 depicts a flow chart for the behavior of the device and a computer system during surface scanning, wherein the objective lens is positioned at position k, and a Z offset is determined and stored, as in an array. Upon sampling a number of positions, the Z offsets are communicated to a computer system, which computes physical offsets, such as by fitting the autofocus offsets to a plane. The physical offsets are communicated back to the sequencing device, which proceeds to acquire 3D imaging data with accurate Z physical offsets. Subpanel 800 depicts a diagram of autofocus Z offsets being fit to a plane for the purpose of determining accurate physical Z offsets.

The practice of the methods disclosed herein may employ conventional biology methods, software, computers and computer systems. Accordingly, the methods described herein may be computer implemented methods in whole or in part. Computer software utilized in the methods of the present disclosure include computer readable medium having computer-executable instructions for performing logic steps of the method of the invention. Suitable computer readable medium include, but are not limited to, a floppy disk, CD-ROM/DVD/DVD-ROM, hard-disk drive, flash memory, ROM/RAM, magnetic tapes, and others that may be developed. The computer executable instructions may be written in a suitable computer language or combination of several computer languages. The methods described herein may also make use of various commercially available computers and computer program products and software for a variety of purposes including obtaining and processing light intensity into data values, automation of reagent delivery, automation of reaction conditions such as thermo-cycling, automation of movement of a stage including a sample holder and a sample and processing and storage of light intensity data and other methods and aspects described herein.

Aspects of the present disclosure are directed to a method of analyzing a plurality of nucleic acids within a three dimensional polymerized matrix including amplifying the plurality of nucleic acids to produce amplicons within the matrix, covalently bonding the amplicons to the matrix, sequencing the plurality of amplicons using an optical sequencing method where the plurality of amplicons are labeled with a detectable label, and volumetrically imaging the plurality of amplicons to produce three dimensional imaging data of the plurality of amplicons wherein light intensity data is processed into a three-dimensional volumetric image. According to one aspect, the plurality of nucleic acids is contained within a biological sample and the matrix-forming material is introduced into the biological sample. According to one aspect, the plurality of nucleic acids is contained within a cell and the matrix-forming material is introduced into the cell. According to one aspect, the plurality of nucleic acids is contained within a tissue sample and the matrix-forming material is introduced into the tissue sample. According to one aspect, the three dimensional imaging data identifies the relative position of the plurality of amplicons within the cell. According to one aspect, the plurality of amplicons is sequenced using fluorescence in situ sequencing. According to one aspect, the plurality of nucleic acids are volumetrically imaged using one or more of 3D structured illumination, selective planar illumination microscopy, light sheet microscopy, emission manipulation, volumetric imaging using pinhole confocal microscopy, volumetric imaging using aperture correlation confocal microscopy, volumetric imaging using volumetric reconstruction from slices, volumetric imaging using deconvolution microscopy, volumetric imaging using aberration-corrected multifocus microscopy, volumetric imaging using digital holographic microscopy.

Aspects of the present disclosure are directed to an automated sequencing and volumetric imaging device including a multi axis stage or positioning system including a sample holder for a three dimensional nucleic acid containing matrix, a heating or cooling apparatus operationally connected to the stage, whereby the heating or cooling apparatus is programmable for time and temperature useful with thermo-cycling for amplification and sequencing, a fluidics dispenser positioned to dispense one or more reagents into the sample holder wherein the fluidics dispenser is in fluid communication with one or more reservoirs for containing one or more reagents, whereby the fluidics dispenser is programmable for dispensing programmed volumes of liquid reagents to the sample holder, a pump operationally connected to the fluidics dispenser whereby the pump forces or withdraws one or more regents from the one or more reservoirs through the fluidics dispenser, an optical assembly including one or more optical axis, one or more detectors positioned in light receiving communication with the sample holder, whereby the one or more detectors receives light intensity signals which processed into a three-dimensional volumetric image of the nucleic acid sample, and one or more microprocessors with software for automating and controlling introduction of reagents into the sample holder, thermocycling of the sample holder, and image detection and acquisition.

REFERENCES

Each reference is incorporated herein by reference in its entirety for all purposes.

Drmanac, R., Sparks, A. B., Callow, M. J., Halpern, A. L., Burns, N. L., Kermani, B. G., Carnevali, P., Nazarenko, I., Nilsen, G. B., Yeung, G., et al. (2010). Human genome sequencing using unchained base reads on self-assembling DNA nanoarrays. Science 327, 78-81.

Islam, S., Kjallquist, U., Moliner, A., Zajac, P., Fan, J. B., Lonnerberg, P., and Linnarsson, S. (2011). Characterization of the single-cell transcriptional landscape by highly multiplex RNA-seq. Genome Res 21, 1160-1167.

Larsson, C., Grundberg, I., Söderberg, O., and Nilsson, M. (2010). In situ detection and genotyping of individual mRNA molecules. Nature methods 7, 395-397.

Larsson, C., Koch, J., Nygren, A., Janssen, G., Raap, A. K., Landegren, U., and Nilsson, M. (2004). In situ genotyping individual DNA molecules by target-primed rolling-circle amplification of padlock probes. Nature methods 1, 227-232.

Shendure, J., Porreca, G. J., Reppas, N. B., Lin, X., McCutcheon, J. P., Rosenbaum, A. M., Wang, M. D., Zhang, K., Mitra, R. D., and Church, G. M. (2005). Accurate multiplex polony sequencing of an evolved bacterial genome. Science 309, 1728-1732.

What is claimed is:

1. A system for nucleic acid analysis, comprising:
a support configured to retain a three dimensional (3D) matrix comprising a plurality of nucleic acid molecules, which plurality of nucleic acid molecules have a relative 3D spatial relationship and are attached to said 3D matrix;
a detector configured to detect a signal from said 3D matrix;
a fluidics dispenser configured to bring a plurality of detectable moieties to said 3D matrix; and
a computer operatively coupled to said fluidics dispenser and said detector, wherein said computer is configured to: (I)(i) direct said fluidics dispenser to bring detectable moieties of said plurality of detectable moieties to said 3D matrix, and (ii) use said detector to detect signals corresponding to said detectable moieties from a plurality of planes of said 3D matrix, and
(II) use said signals detected by said detector to generate a 3D volumetric representation of said plurality of nucleic acid molecules, which 3D volumetric representation identifies said relative 3D spatial relationship of said plurality of nucleic acid molecules.

2. The system of claim 1, further comprising an optical assembly comprising said detector, which optical assembly is configured to adjust a position of said detector relative to said support to detect said signals from said plurality of planes of said 3D matrix.

3. The system of claim 2, wherein said optical assembly comprises one or more objective lenses that are configured to be in optical communication with said support.

4. The system of claim 1, further comprising a track and a motor having an encoder feedback for adjusting a position of a focal plane of said detector.

5. The system of claim 1, further comprising a mapping unit configured to map a surface of said support with respect to one or more motion axes such that said 3D matrix is reproducibly positioned relative to said support.

6. The system of claim 5, wherein said mapping unit comprises a focusing unit that is configured to acquire one or more distance measurements between said detector and said 3D matrix.

7. The system of claim 5, wherein said mapping unit is configured to compute one or more offsets relative to a positional encoder along said one or more motion axes.

8. The system of claim 1, further comprising a heating or cooling unit operatively coupled to said support and configured to subject said plurality of nucleic acid molecules to thermo-cycling.

9. The system of claim 1, wherein said plurality of planes is a plurality of focal planes of said detector.

10. The system of claim 1, wherein a position of said detector relative to said support is adjustable for detecting said signals from said plurality of planes.

11. The system of claim 1, wherein said computer is configured to use said signals detected in (I) to identify sequences of said plurality of nucleic acid molecules or derivatives thereof, and wherein said 3D volumetric representation of said plurality of nucleic acid molecules identifies said sequences.

12. The system of claim 1, wherein said detector is configured to detect said signals from said plurality of planes as a hologram.

13. The system of claim 1, wherein said detector is configured to detect said signals from said plurality of planes simultaneously from said plurality of planes.

14. The system of claim 1, wherein said detector is configured to detect said signals from said plurality of planes sequentially across individual planes of said plurality of planes.

15. A method for nucleic acid processing or analysis using the system of claim 1, comprising:
(a) providing said three dimensional (3D) matrix comprising said plurality of nucleic acid molecules on said support, which said plurality of nucleic acid molecules have said relative 3D spatial relationship and are attached to said 3D matrix;
(b) while said plurality of nucleic acid molecules or derivatives thereof are coupled to said 3D matrix, and with the aid of said computer, (i) direct said fluidics dispenser to bring said detectable moieties to said 3D matrix, and (ii) using said detector to detect said signals corresponding to said detectable moieties from said plurality of planes of said 3D matrix; and
(c) with the aid of said computer, using said signals detected by said detector in (b) to generate said 3D volumetric representation of said plurality of nucleic acid molecules, which 3D volumetric representation identifies said relative 3D spatial relationship of said plurality of nucleic acid molecules.

16. The method of claim 15, wherein said plurality of nucleic acid molecules is from a cell.

17. The method of claim 15, wherein said plurality of nucleic acid molecules is covalently coupled to said 3D matrix.

18. The method of claim 15, further comprising, prior to (a), (I) providing a biological sample comprising said plurality of nucleic acid molecules, (II) introducing a matrix-forming material into said biological sample, and (III) using said matrix-forming material to generate said 3D matrix.

19. The method of claim 18, wherein said biological sample is a cell.

20. The method of claim 19, wherein said 3D matrix is in said cell, and wherein in (b) said signals are detected from within said cell.

21. The method of claim 20, wherein said signals are optical signals.

22. The method of claim 18, wherein said biological sample is a tissue.

23. The method of claim 15, wherein said 3D matrix comprises a polymeric material.

24. The method of claim 15, wherein said signals are detected at a plurality of planes within said 3D matrix simultaneously.

25. The method of claim 15, wherein said signals are detected while said derivatives thereof detectable moieties are brought to said 3D matrix.

26. The method of claim 15, further comprising using said signals detected in (b) to identify sequences of said plurality of nucleic acid molecules or derivatives thereof.

27. The method of claim 26, wherein said 3D volumetric representation identifies said sequences.

28. The method of claim 15, wherein said detectable moieties are detection probes having sequences, and wherein (b) further comprises (I) contacting said plurality of nucleic acid molecules or derivatives thereof with said detection probes to permit said sequences of said detection probes to couple to sequences of at least a subset of said plurality of nucleic acid molecules or derivatives thereof, and (II) identifying said sequences of said detection probes to identify said sequences of said at least a subset of said plurality of nucleic acid molecules or derivatives thereof.

29. The method of claim 15, wherein said 3D matrix is disposed adjacent to a stage, and wherein in (b) a position of said detector relative to said stage is adjusted to detect said signals from said plurality of planes.

30. The method of claim 15, wherein said plurality of planes is a plurality of focal planes of said detector.

31. The method of claim 15, wherein (a)-(c) are performed in an absence of physical sectioning of said 3D matrix.

32. The method of claim 15, wherein said detector detects said signals from said plurality of planes as a hologram.

33. The method of claim 15, wherein said detector detected said signals from said plurality of planes sequentially across individual planes of said plurality of planes.

34. The method of claim 18, wherein (a)-(c) are performed in an absence of physical sectioning of said biological sample.

35. The method of claim 15, wherein, in (b), a first signal of said signals is detected prior to a second signal of said signals.

36. The method of claim 15, wherein said 3D matrix is not derived from formaldehyde.

37. The method of claim 15, wherein said 3D bmatrix is not derived from an embedding wax.

* * * * *